(12) United States Patent
Danisch et al.

(10) Patent No.: US 6,563,107 B2
(45) Date of Patent: May 13, 2003

(54) TOPOLOGICAL AND MOTION MEASURING TOOL

(75) Inventors: Lee Allen Danisch, Upper Kingsclear (CA); Jonathan Freeman Danisch, Upper Kingsclear (CA); Jordan Patrick Lutes, Fredericton (CA)

(73) Assignee: Canadian Space Agency, Saint-Hubert (CA)

( * ) Notice: Subject to any disclaimer, the term of this patent is extended or adjusted under 35 U.S.C. 154(b) by 103 days.

(21) Appl. No.: 09/757,698

(22) Filed: Jan. 11, 2001

(65) Prior Publication Data

US 2002/0088931 A1 Jul. 11, 2002

(51) Int. Cl.$^7$ .................................................. G01J 1/04
(52) U.S. Cl. ............................ 250/227.14; 250/227.16; 385/13
(58) Field of Search ..................... 250/227.11, 227.14, 250/227.16, 227.24, 227.28, 221, 224; 385/12, 13; 356/73.1; 340/555, 556, 557; 600/595

(56) References Cited

U.S. PATENT DOCUMENTS

| | | | |
|---|---|---|---|
| 5,182,779 A | 1/1993 | D'Agostino et al. ........... 385/13 |
| 5,481,922 A | 1/1996 | Washabaugh ................. 73/774 |
| 5,694,497 A | * 12/1997 | Dansone ....................... 385/13 |
| 6,127,672 A | * 10/2000 | Danisch ................... 250/227.14 |

\* cited by examiner

*Primary Examiner*—Kevin Pyo
(74) *Attorney, Agent, or Firm*—David J. French

(57) ABSTRACT

A measuring device for providing data corresponding to a geometric configuration in space, in the form of a flexible, compliant, measurement member capable of bending in at least one degree of freedom and extending along a medial axis or plane. The member has spaced flexure sensors distributed at known locations on the member and separated by known sensor spacing intervals to provide flexure signals indicating the local state of flexure present at the locations. The member comprises a multiplicity of formed, i.e. shaped, fibers, these fibers including sensing fibers having sensing portions which provide the flexure sensors, the sensing portions of different fibers being located at differing distances along the member so as to be located at the sensor spacing intervals, the formed fibers being in mutually supporting relationship, as by continuous or repeated contact with each other. Such fibers may constitute most or all of the member.

39 Claims, 18 Drawing Sheets

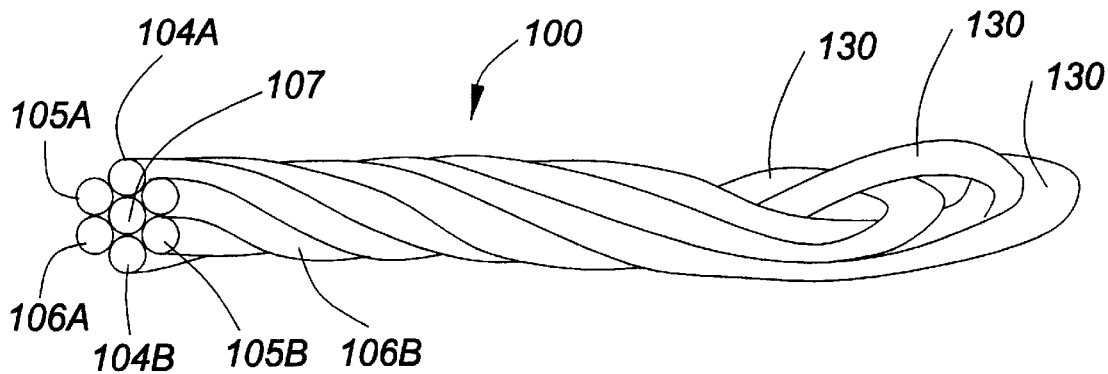
FIG. 24
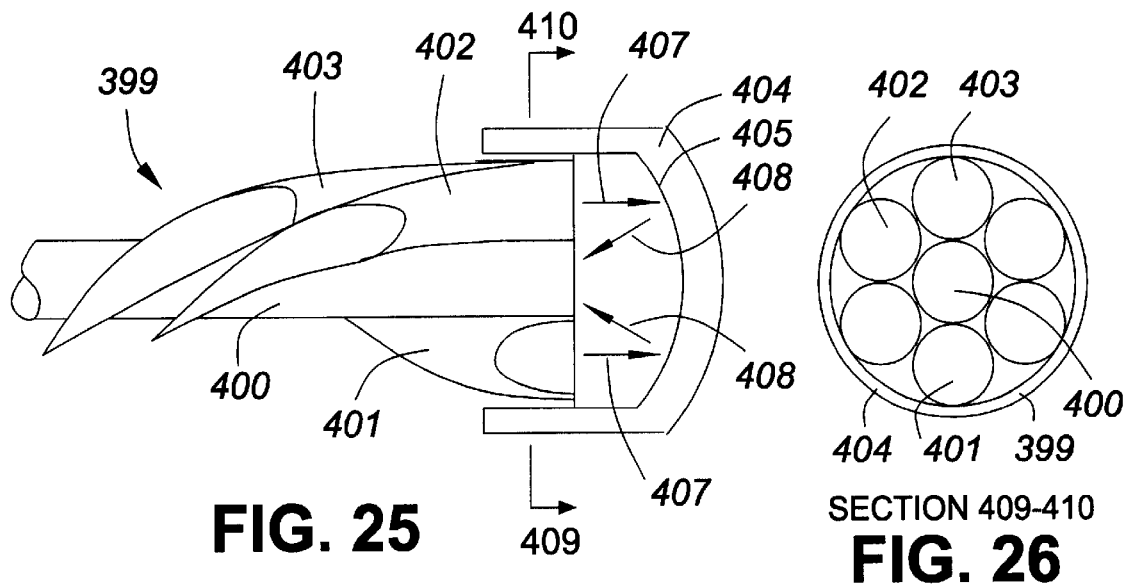
FIG. 25
SECTION 409-410
FIG. 26
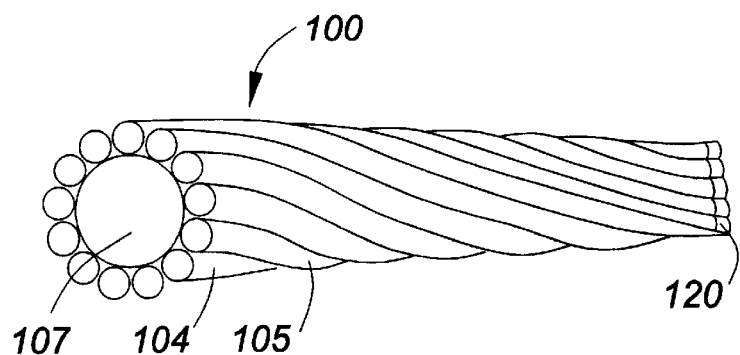
FIG. 27

SECTION 135-135

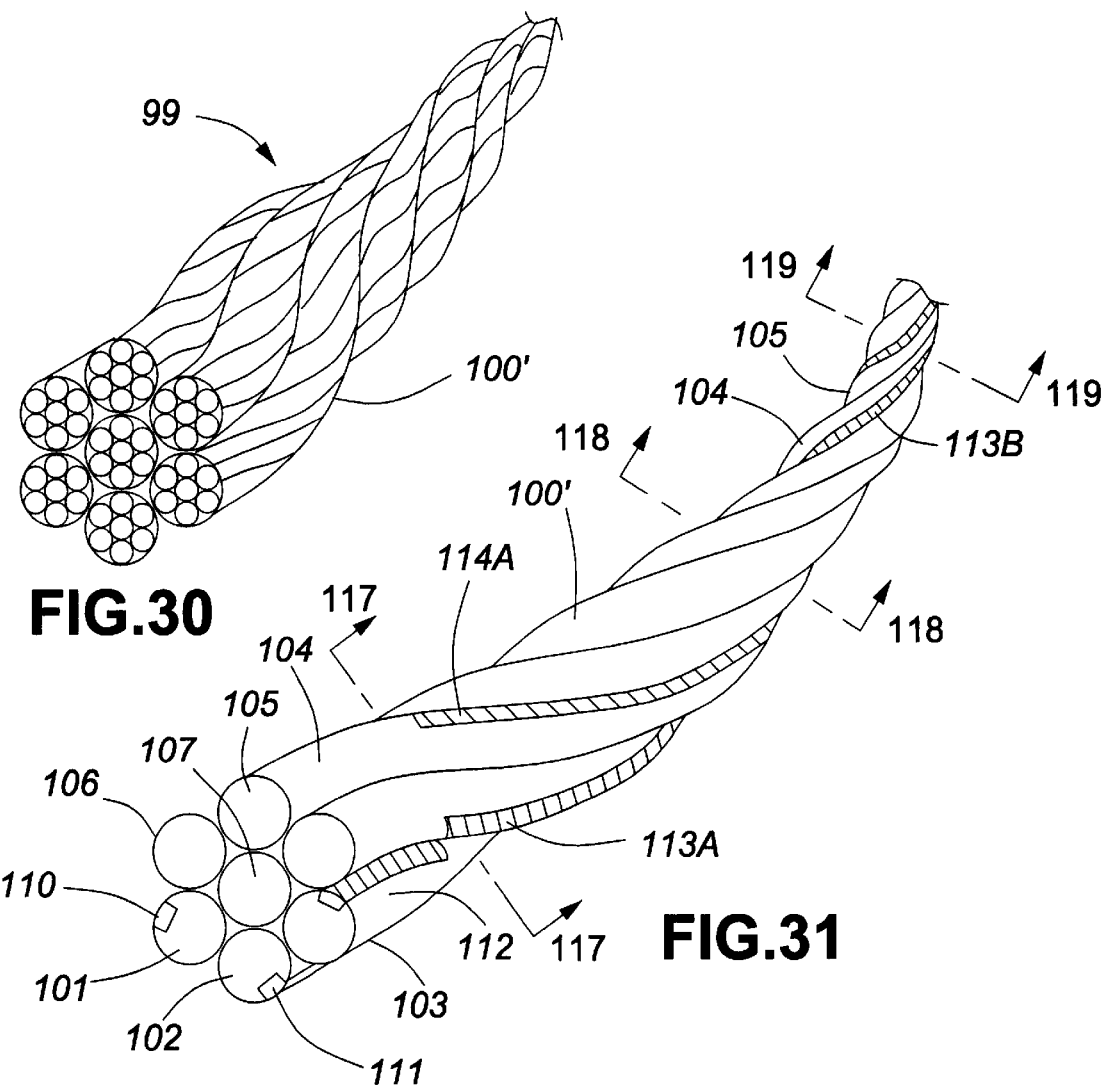
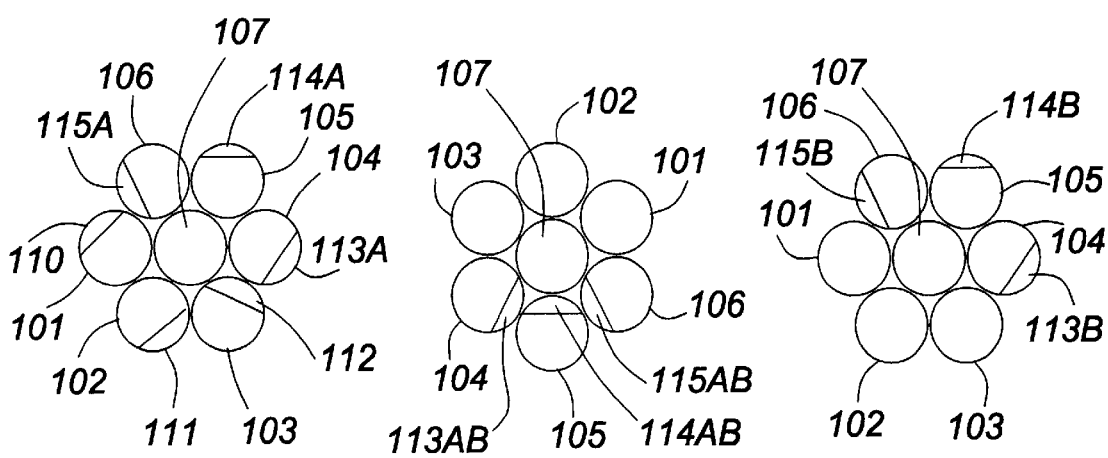
SECTION 117-117
FIG.32
SECTION 118-118
FIG.33
SECTION 119-119
FIG.34

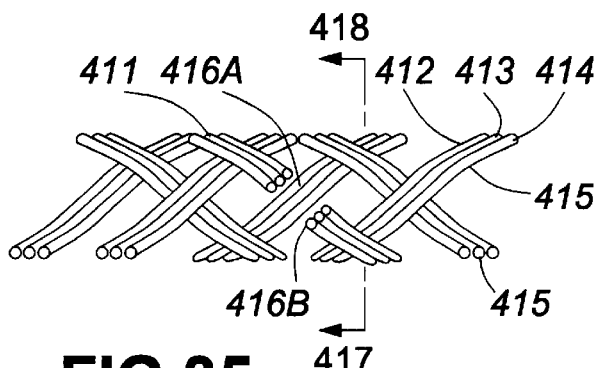
FIG.35
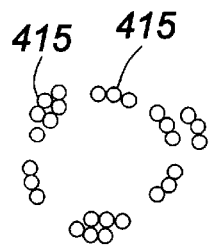
FIG.36
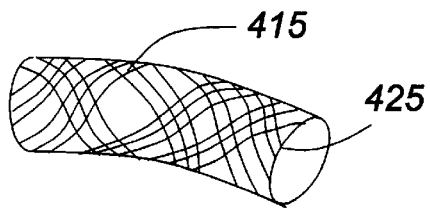
FIG.37
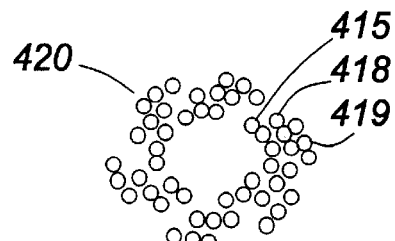
FIG.40
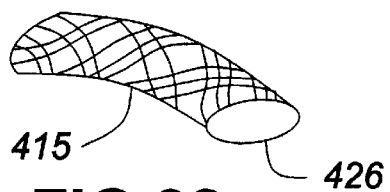
FIG.38
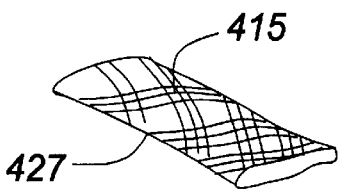
FIG.39
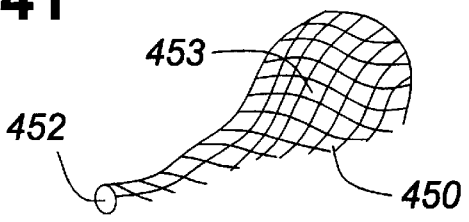
FIG.41
FIG.42

TOPOLOGICAL AND MOTION MEASURING TOOL

FIELD OF THE INVENTION

This invention relates to sensor technology. In particular, the invention relates to a tool or device for measuring the geometric location and configurations of objects in space. The invention is suited to robotic applications and to monitoring or measuring human geometry and motion. This invention represents modifications and improvements in the inventions described in U.S. Pat. No. 6,127,672, issued Oct. 3, 2000 to Lee Danisch, and PCT Appln. No. PCT/CA98/00213, published as WO98/41815, which are both incorporated by reference.

A preferred application, amongst others, is in the field of animation effected by motion capture of movements by the human body.

BACKGROUND TO THE INVENTION

Various technologies have been applied to measure the location, orientation and surface shapes of objects in space.

In the field of robotics it is known to determine the location of a flexible member formed by a series of rigid, linked elements in space by measuring the angular degree of rotation existing at the various joints joining such linked elements.

Rotations in a flexible member include bending that is transverse to the longitudinal extent of the member; and twisting that occurs about an axis which is coincident with the longitudinal extent of the member. Both types of movement or distortions qualify as "flexures".

Twist is usually negligible in sensor structures based on cylinders, rods, and other solids with significant cross-sectional dimensions. However, it can be very advantageous to measure the presence of twist in elongate, flexible members that are rope-like in their flexibility. Such members would be very convenient for incorporation in garments.

Thus one object of the present invention is to provide an improved flexible member or reference platform equipped with distributed sensors wherein changes in the shape of the member are sensed by the sensors in such a way that the complete shape of the member can be found by calculations from the outputs of the sensors.

Another object of this invention is to provide an instrumented flexible member that is sufficiently compliant to substantially conform to the surface of a curved object and act as a sensor to provide electronically processable data as to the shape of that surface.

A variety of sensors exists for measuring the state of flexure—bend and twist—in an object; these include optical fibers and conductive metal fibers, i.e. wires. A convenient class of sensors particularly suited to this objective relies on fiber optics.

U.S. Pat. No. 5,321,257 to Lee Danisch, describes modified optical fibers that are provided with a light absorbent region on a portion of the outer fiber surface, especially on one selected side of the outer fiber surface, such region providing a bend sensor whereby the curvature at such modified region may be remotely detected by the change in the overall light transmission capacity of the fiber. This prior patent depicts, in FIG. 12, the deployment of clusters of modified fibers capable of detecting a bend at a particular location in three dimensional space. The associated fiber ends are all connectable at one end to a multi-fiber light source, light sensing and signal processing unit. These modified fibers, or so-called "bend enhanced fibers", are referenced in the aforesaid '672 patent.

The aforesaid U.S. Pat. No. 5,531,257 also discloses three optic fiber sensors mounted in parallel, with the sensors being sensitive to bending in separate directions, and which are used for resolving bends in multiple DOFs in a flexing structure. However, this prior patent does not suggest any method of dealing with twist, which would cause ambiguity or be undetectable in the readings of the patented sensor method of this '257 patent. Accordingly, this patent does not deal with the problem of determining the complete position and orientation of a longitudinally extended structure based only on measurement of flexure.

Another problem with this simple structure is that when three straight fibers are bent, some will be extended and some compressed, due to difference in radius of curvature, which leads to significant errors in measurement.

A further paper on this subject by the inventor herein entitled "Laminated Beam Loops" has been published in SPIE Vol. 2839, pp. 311–322, 1996. The contents of this paper, the above referenced United States patents and the published PCT application PCT/CA94/00314 are all incorporated by reference herein.

Optical fiber sensors can measure bend and, in accordance with the invention described in the aforesaid '672 patent, twist, based on the disposition of the fiber and the location of the treated, light absorbing region of the fiber surface along the fiber. The sensitive region of the fiber can be contained within a running length of on the order of three millimeters to many centimeters for example 30 cm, depending on desired sensitivity and the dimensions of the fibers. This provides a corresponding span for the sampling of the average state of curvature of the sensing region of the optic fiber. Fiber optic technology is convenient for use in sensors because it is robust, benign and inexpensive. The aforesaid '672 patent describes various forms of measuring tools which incorporate bend and twist sensors, of which the preferred forms are fiber optic based sensor systems that can provide remote information on the locations of objects in space, the shape of surfaces and changes in the shape of surfaces. However, the '672 patent is not limited to fiber optic based sensors. Similarly, while the present invention will also be described principally in relation to fiber optics sensors, it is not limited to systems using such sensors.

The invention of the U.S. '672 patent, according to one aspect, is a shape and position measuring tool which comprises the following features:

1. a longitudinally extending, flexible substrate having a compliant reference surface and being capable of bending in at least two degrees of freedom so as to be configurable in three dimensional space;
2. a plurality of spaced bend sensor means and a plurality of spaced twist sensor means each of said plurality of sensor means being respectively coupled to and positioned at specific discrete locations, on and at known respective bend sensor and twist sensor spacing intervals along the longitudinal extent of the substrate, to provide flexure signals indicating the respective local state of bend and twist present in the substrate at the respective locations where the respective bend sensor means and twist sensor means are coupled to the substrate;
3. sensor data processing means coupled to the bend sensor means and the twist sensor means for receiving signals therefrom and for presenting data on the geometric configuration of the reference surface of the substrate in three-dimensional space, wherein the sensor data processing means operates by determining the geometric configuration of the substrate from the bend and twist signals derived from the flexure signals provided by the bend sensor means and twist sensor means at their specific locations and from the spacing intervals between such sensor means.

As indicated, the shape measuring tool of the '672 patent included a flexible substrate which carried the bend and twist sensors at specific locations on the substrate. The substrates included ribbons (FIGS. 5, 6 and 8), and ropes (FIG. 7). Substrates of sheet form were also contemplated, including a planar array with substantial width as well as length, for example a "keyboard" type of device.

The present invention is based on similar principles, but with the omission or minimization of the presence of a substrate for the support and positioning of flexure sensors.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

It has now been found possible and in some cases advantageous to construct flexible members similar to those described in the '672 patent but wherein there is no substrate, or only a minimal substrate, additional to the fibers which provide the sensors.

Accordingly, the present invention provides in one aspect a measuring device for providing data corresponding to a geometric configuration in space, the device in one aspect being in the form of a flexible, compliant, measurement member capable of bending in at least one degree of freedom, the member extending along a medial axis or plane and having spaced flexure sensors distributed at sensing locales having known locations on the member and separated by known sensor spacing intervals to provide flexure signals indicating the local state of flexure present at said sensing locales.

According to one embodiment the measurement member comprises a multiplicity of formed fibers, as defined below, said formed fibers including sensing fibers having sensing portions which provide said flexure sensors, the sensing portions of different fibers being located at sensing locales at differing distances along said member so as to be located at said sensor spacing intervals, said formed fibers being in mutually supporting relationship, the overall form of the measurement member being substantially maintained by the form of the constituent fibers themselves or by their continuous or repeated contact with each other to enhance the strength or stability of the member. The fibers may have continuous or repeated connections with each other, such as by being interwoven or entwined to provide dimensional stability. Alternately, the fibers may be sufficiently rigid to be self-supporting without inter-fiber contact. The "form" of the device refers to the organization and placement of the fibers with their sensing portions, allowing that measuring device is, overall, flexible and capable of conforming to various shapes in space.

Such fibers are preferably obliquely deployed or formed in the sense that their sensing portions are obliquely oriented with respect to the extent of the member itself.

The term "fiber" in this context means an element of a member with primarily axial extent, its path describable by a space curve, which is a well-defined mathematical entity with mathematically defined bend and twist. The term "fiber" includes an element of polygonal cross-section.

The term "obliquely formed" in relation to fibers, or "obliquely oriented" in relation to sensing portions, means being non-straight or non-aligned with the medial axis or plane of the member when the medial axis or plane of the member is straight or flat, i.e. fibers have a two-dimensional or three-dimensional form when the overall member is straight or flat. These formed fibers are normally deployed in a cyclical or repeating pattern. Formed fibers may either be fibers such as optical fibers which have been heat treated while being deformed so as to have a permanent shape, or they may be non-straight merely by virtue, for example, of being twisted into the form of a rope or knitted or woven into a textile.

Formed fibers have the following useful properties for this invention:

a) Formed fibers have an ability to support each other by repeated contact or repeated connections amongst the fibers and along the member constituted by the fibers. This ability to support each other despite flexure of the member in one or more degrees of freedom preferably persists over a large angular range of both bend and twist. The mutual support between the fibers, which gives the member an integral structure, distinguishes the member of this invention from:
  1) a mere bundle of loose fibers, and
  2) multiple straight fibers held in a non-planar bundle by adhesives b) The formed fibers can readily form cyclical structures, i.e. structures with repeating patterns, for example ropes, ribbons formed by adjacent wavy fibers, and woven or knitted textile type structures. Such structures may have cyclically repeating curves that take on cyclically repeating pairs of opposed deformations locally within each curve during curvature of the measuring device, without substantial changes in the net extension or compression of the fibers along the full extent of the device whereby said curvature can occur without overall slippage of fibers along their full length. Preferably, the fibers are optical fibers with loss zones having a circumferential orientation and axial placement along each fiber, said orientation and axial placement producing a desired circumferential orientation and axial placement of light loss with respect to the device resulting from the formed curves of the fibers, such that the loss geometry produces modulation of the light indicative of the position and orientation of the device.

c) Structures made of the formed fibers have an ability to flex over a large range of bend and twist without significantly slipping past each other either locally or over their complete extent, and without a substantial net extension or compression of the fibers axially along the member. When used in a rope, out-facing waves of one fiber are extended under tension, while in-facing waves of the same fiber compress, with the net extension being zero. Local slip is minimal and can be designed to be within the elastic limits of an adhesive, if any is used.

As an example of a two-dimensional (when flat) form of the invention, a multiplicity of formed fibers in the configuration of a wavy ribbon (wavy within its plane) may be used as a measurement instrument. Such ribbon may be affixed to a moving body and will follow the movements without buckling, because the formed waves are able to bend slightly within the plane of the ribbon throughout their lengths, thereby absorbing length differences inherent in measurements outside the neutral axis of a body. Similar attachment of an unwaved ribbon will result in buckling of the ribbon during axial compression. The waves also permit sensing of twist, which is impossible if the fibers are purely axial in lay.

Another aspect of the invention when the member is of an undulating or cyclical form is that flexure results in changes in the proximity (edge-to-edge) and register (axial loci change relative location axially along the fibers) between adjacent cycles of the formed shape, for example a helical shape. This occurs in cyclical fashion along the overall member, without an overall change in length of the fibers.

d) Formed fibers according to the invention provide the ability to sense twist, since the fibers have sensing portions which are obliquely oriented to the axial direction or plane of the member. A suitable structure may be made particularly sensitive to twist by having a wind-up/wind-down portion of the member that has extra twist present over a limited span that includes sensing portions. Such a structure may be tailored to be minimally responsive to bend, by adjustment of the extra-twist portion. A twist-sensitive portion of fiber gives a maximum response if oriented 45 degrees to the medial axis or plane of the member.

e) the invention provides a means of treating the fibers in their formation so that the imposed form imparts to treated zones desired three dimensional angular orientations within the member and bipolar response to curvature of the member. This can be made to occur even if the same zones had only axial orientation and unipolar response to curvature, when straight and flat.

In some circumstances, all the formed fibers extend substantially the full length of the member. In fact, the member may be made up entirely or largely of the formed fibers, so that the stiffness of the member is not substantially greater than the combined stiffness of the fibers. Similarly, the formed fibers may provide the major part of the tensile strength of the member. In particular cases, formed optical fibers which are sensing fibers, i.e. have sensing portions, may constitute a large portion, or virtually the whole of, the member.

It will be shown in this disclosure that cyclical structures enable an advantageous interplay between the cyclical form and the functions required of sensors on the fibers. These advantages hold even for structures that do not support each other as in a) above, but rather are relatively stiff so that the structure is a grouping of cyclical fibers held in interrelation by end supports. An example is three helixes like helical springs with a common central axis, held at the ends, for example, by disc-shaped plates, but that do not touch each other. Such a structure can bend and twist, has formed fibers, and provides an improved platform on which to place sensors. These structures are distinguished over the prior art in part by the fact that at least most of the formed fibers extend substantially the full length of the member so as to contribute materially to the strength of the member, and in one variant, no structure other than the fibers is necessary to maintain structural integrity.

In some cases, formed fibers, including sensing fibers, may make up most or all of an elongated member, but not all the formed fibers need extend the full length; this results in a tapered member in which each fiber extends just as far as is necessary along the member, to the point where it is required to sense bending or twist.

Generally, the member is elongated and the sensors are spaced along the member at said locations. In order to measure twist as well as bending, portions of at least some of the fibers which constitute the sensors are obliquely orientated to the longitudinal dimension of the member, preferably at 45 degrees, to the member medial axis for an elongate member. However, the member may also be in the form of a flexible sheet, with the sensors spaced all over the sheet. In such case, the sensing portions of at least some of the fibers are obliquely oriented either with respect to each other or with respect to the plane of the member.

For the elongated member, the invention works by sampling curvature at multiple, spaced intervals along the elongated member. The invention relies upon inter-referencing the position of flexure sensors located at known intervals along the member with the location of adjacent sensors so that the location of all sensors with respect to each other is known.

Bend can be measured about either one or two axes that are orthogonal to the longitudinal dimension of the member, depending on the nature of the member. Thus a measurement member of rope-like form would require that bending be sensed about two such axes, either directly or indirectly.

By providing a member which is deformable only in restricted degrees of freedom, the number of sensors required can be reduced. In one preferred configuration, the member is in the form of a ribbon formed of a series of fibers, for example optical fibers, connected together side-by-side. In such case bend sensors may be the only sensors required for measuring flexure of the ribbon in its permitted bending mode. This reduces the number of bend sensors needed per unit of length.

A ribbon is an article which is substantially limited to bending along its length about axes which are transverse to the longitudinal dimension of the ribbon and within the plane of the ribbon, while the ribbon remains free to twist about its longitudinal dimension. Thus a single bend sensor will suffice to measure bend at a location along a ribbon. To complete the definition of the geometric configuration of the ribbon-like member, twist must also be measured by twist sensors located at known intervals along the longitudinal extent of the length of the ribbon. Such bend and twist sensors may be interspersed with each other or be co-located along the ribbon. The ratio between such types of sensors may depart from a strict ratio of 1:1. Furthermore, in many cases each individual sensor is responsive to two or more degrees of freedom, such as two degrees of freedom of bend and one of twist, and the degrees of freedom are separately determined by mathematical operations involving all of the sensors in a similar region.

When the member is of a ribbon-like configuration employing both bend and twist sensors, freedom of movement and tracking of the geometric configuration of the ribbon in three dimensional space is nevertheless available. This is because the ability of a ribbon to twist allows portions of the ribbon to be re-oriented in any direction in space.

An elongated configuration for the invention can also be implemented by applying an instrumented planar fibrous tape of fibers assembled in the ribbon-type format helically to the outside, or inside, of a cylindrical flexure of resilient material, for example a hose. When a hose-like carrier is employed, sensor communications may pass through the core. While a carrier may contribute to the strength or stability of the member, the oblique orientation of the sensing portions of the fibers allow for bend and twist conditions to be monitored along the length of the member.

The fibrous tape in such case contributes materially to the overall strength or stability of the composite member, preferably the greater portion. In the case of a helically coiled fibrous tape or ribbon, according to the invention, used in conjunction with a tubular carrier, counter-rotating helical components may be combined as in the structure of a) braided rope, or b) a layer wound clockwise, surmounted by a layer wound counterclockwise. This further enhances the mechanical stability of the structure, such as making it resistant to twisting.

The invention is an improvement over previous forms in that the fibers are either a) on the neutral axis of the member as in the case of a ribbon with side-by-side fibers or b) bend and twist without net elongation as in the case of rope and tube forms where outward-facing curves extend and inward-facing curves compress during curvature of the member.

Where the bend and twist sensors are sensing portions of optical fibers that have been rendered sensitive to their state of curvature as described above, the optical fibers which form the member, or a main part of the member, will usually have only one such sensing portion on each fiber, the positions of which are strategically arranged to sense bending at appropriate places on the member. However, the light sensing portions may be made specific to certain light wavelengths, and may be connected to light source and signal processing units which provide the different wavelengths and which distinguish between them, in which case each fiber can have several light sensing portions at different positions along its length and can produce information relating to bend at the different positions.

In the case of a ribbon that is generally constrained to exhibit bending about axes extending transversely to the ribbon's length, the sensors may be portions of optical fibers that are aligned parallel to the plane of the ribbon and in the direction of its longitudinal length at the locations where bending information is required. The sensing portions of an optical fiber may be generally aligned to lie across the axis about which bending is to occur, e.g. the axes extending transversely to the length of a ribbon.

For convenience of signal processing in a ribbon member, both twist and bend at a single location can be measured using two bend sensors having their bend sensing portions oriented at angles with respect to each other. These bend sensors may or may not be looped optical fibers, as described in PCT Application PCT/CA94/00314 (published as WO 94/29671), and in the aforesaid '672 patent. The directions of the sensing portions of the pair of fibers are preferably oriented at substantially the same angle off the longitudinal median line of the ribbon member and preferably at 45 degrees to the longitudinal dimension of the member for maximal effect. This permits two fibers to be used to measure both bend and twist at a single location by processing their outputs to extract their sum and difference signals as a measure of twist or bend. The referenced angular orientations simplify signal processing. With computational adjustments other angles would still be able to provide both twist and bend values from a splayed pair of sensors. Since the sensors will normally be operated in their linear ranges, the computations normally involve sums and differences of linear equations which are very amenable to high speed automatic computation.

By assembling distributed sets of sensors, flexure sensing regions may be formed not only linearly, as along a supporting rope or ribbon-like member, but also over an area of a flexible sheet-like member. The sensor portions can be in groups and can consist of bend and twist sensors, or dual-direction bend sensors, which are able to completely describe the shape of the sheet. Using data on the state of curvature at each sensing region, and knowing the separation between sensors, the signal detection system can construct a depiction of the shape of the sheet. With the sheet placed in contact with a geometric surface of unknown form, the shape of such surface can be measured, at least where the sheet and surface are in contact.

In all forms, the sensors for bend need not be co-located with the sensors for twist, and/or bend sensors need not be co-located with their differently oriented bend sensing mates. It is sufficient for them to be distributed along the member at known intervals that allow the configuration of the member to be determined.

Although most references herein have been made to inextensible flexures, extensibility can be allowed to exist in the member. Thus, a possible form of the invention could be a stretchable member wherein not only bend and possibly torsion are measured but also extension. The degree of extension must be detected to ensure that the spacings between the flexure sensors will be known. Extension sensors could include portions of conductive elastomers sensitive to extension. For convenience and to improve compliance, extension could be limited to a small increase in length beyond which the flexure becomes functionally inextensible. Alternatively, in a 'doubly formed embodiment', a sensor body with an elongate form (e.g. a tape, rope, rod, etc.) containing formed fibers with loss zones to sense its bend and twist is further formed (e.g. by heat treatment or adhesives) to follow a sinuated path, e.g. a helical path. The extension and compression of the resulting doubly formed member will be measured along with the other details of its shape as a consequence of measuring the aforesaid bend and twist and thereby determining position and orientation of all portions of the elongate sensory member.

In sensing members of this invention, formed largely or entirely of formed fibers, one of the most useful forms for bend and twist sensing is the helix, which is a cyclical 3 dimensional structure defined by constant bend and twist along its length when undeformed (unbent). Other useful forms for sensing members of the invention include loops and waves which are primarily 2 dimensional structures. Cyclical flexures provide many opportunities for exploiting shape sensing.

Many constructions are based on the helical form. A good example is rope, which comprises fibers wound into strands, which are in turn wound into the rope. The elastic tendency of the fibers to unwind from the strands is counteracted by winding the strands into rope in a direction opposite to that used to wind fibers into strands. Then any unwinding of the fibers tends to tighten the strands within the rope. Forces and moments within the system reach equilibrium to maintain the structure of the member. Another example of use of the helical form is the helical covering for wires and cables, formed from a bent and twisted band of metal or plastic.

Ropes, and other helical forms, are examples of cyclical members or flexures made up of formed fibers which provide repeating zones with similar orientations. This allows bend or twist sensing to be distributed along an extent of a single sensor fiber (or pair, or triplet, or larger subset of fibers at a known location) of a larger array of such subsets. The single sensor or grouping can take on the repeating characteristic, such as an orientation of 45 degrees to an axis, without requiring that all the fibers forming the entire member have that orientation.

Most cyclical structures provide flexibility while permitting significant lateral deflections. This is true of sinuous ribbons, ropes, and textiles (2D elongate, 3D elongate, and 2D or 3D elongate or planar structures respectively). A sinuous or wavy ribbon, i.e. wavy within its plane, which may be made by glueing sinuous fibers together, will be able to extend and compress during flexing of the body because the individual waves can extend and compress by bending within their planes. A helical rope can be twisted into a larger helix and a sinuous ribbon can also be twisted into a helix. The lateral deflections provided by cyclical structures are useful when the sensor must surround another body, such as a flexible endoscope whose shape is to be sensed, or carry elements such as wires or return fibers within its structure, or when the sensor has a multiplicity of fibers or wires that take up space. The combination of flexibility and lateral deflectability may be exploited to a high degree in sinuated, looped, and helical structures.

Ropes and textiles were invented millenia ago to conform to arbitrary surfaces, and employ the same sinuations, loops, helixes, braids, and woven or knitted elements that will be demonstrated herein for sensor structures which use formed fibers at least some of which are sensing fibers. Significant improvement over straight fibers attached to flexible substrates is effected by the use of cyclically repeating, sinuous fibers that form a sensing member through interrelationship without a separate substrate. Examples include ropes and textiles with sensing capabilities along the fibers.

Unless the sensing fibers (optical, wire, etc.) are at the neutral axis, some slippage between the fibers and any substrate used, in addition to the fibers, must be permitted to occur or bend and twist sensing will be compromised. This is because a length change must be accommodated for any in-extensible/incompressible flexure lying against or upon another similar flexure, when both are bent: both flexures can accommodate the same radius of curvature only if allowed to slip one upon the other. If slip is not allowed to occur, either one of the fibers will buckle in compression at the point of weakest attachment, or bend in a plane will be converted to twist or out-of-plane bending of the fiber. These problems can largely be avoided by forming the member from the fibers themselves, without any additional substrate.

The foregoing summarizes the principal features of the invention and some of its optional aspects. The invention may be further understood by the description of the preferred embodiments, in conjunction with the drawings, which now follow.

SUMMARY OF THE FIGURES

FIG. 24 is a side view of a rope having looped optical fibers;

FIG. 25 shows the end of an optical fiber rope member having a mirror to return light through a central fiber;

FIG. 26 shows a cross-section through the end of the rope of FIG. 25;

FIG. 27 shows a perspective view of a rope having a central core;

FIG. 28b shows a detail of a capacitance sensing groove on one of the fibers from FIG. 28a.

FIG. 28c shows layers of one of the fibers from FIG. 28a.

FIG. 28d shows portions of coupling grooves on two adjacent fibers from FIG. 28a.

FIG. 30 shows a perspective view of another rope formed of optical sensor fibers;

FIG. 31 shows a similar view of one of the strands of the rope of FIG. 30;

FIGS. 32, 33, and 34 show cross-sections through the strand of FIG. 31;

FIG. 35 shows a braided structure formed of optical sensing fibers;

FIG. 36 is a cross-sectional view of the FIG. 35 structure;

FIG. 37 is another view of the FIG. 33 structure;

FIGS. 38 and 39 show structures similar to FIG. 35 but of different shapes;

FIG. 40 shows a cross-section through another braided structure;

FIG. 41 shows a hollow woven structure formed of optical sensing fibers;

FIG. 42 shows a similar structure with a closed end;

DESCRIPTION OF THE PREFERRED EMBODIMENTS

Figure 1:
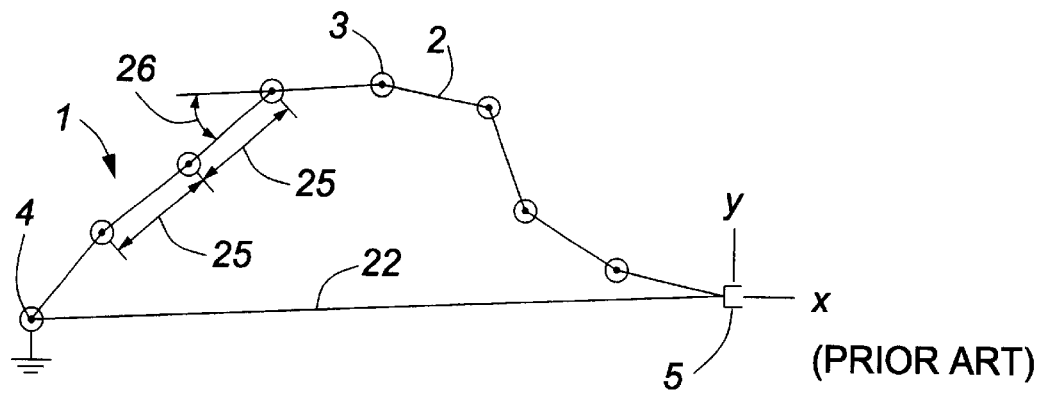
FIG. 1 is a schematic of a prior art planar mechanism composed of rotary bending joints and links provided with joint sensors whereby the location in space of the distal end with respect to the base end can be determined.

FIG. 1 represents a prior art mechanism 1 in the form of rigid links 2 that are coupled at joints 3 that have parallel axes. This mechanism 1 is therefore free to move or bend in a single plane. It is anchored to a reference point 4 at one end and may have an end effector 5 at its other end. All of the joints 3 are instrumented to have sensors (not shown) which provide information as to the angular orientation of the joints 3.

It is possible by processing the signals from the sensors and knowing the lengths of each of the links 2 to determine by calculation the distance to and position of the end effector 5 in space with respect to the reference point 4. In fact, the positions of all joints 3, and locations therebetween on specific links 2, can be calculated by interpolation.

With rigid links and mechanical joints it has not been possible in the past to multiply such elements to a number which is large enough to provide a shape or position measuring tool which has a high capacity for compliance with an irregularly curved surface. Further, the mechanism of FIG. 1 is limited to motion in a single plane.

Figure 2:
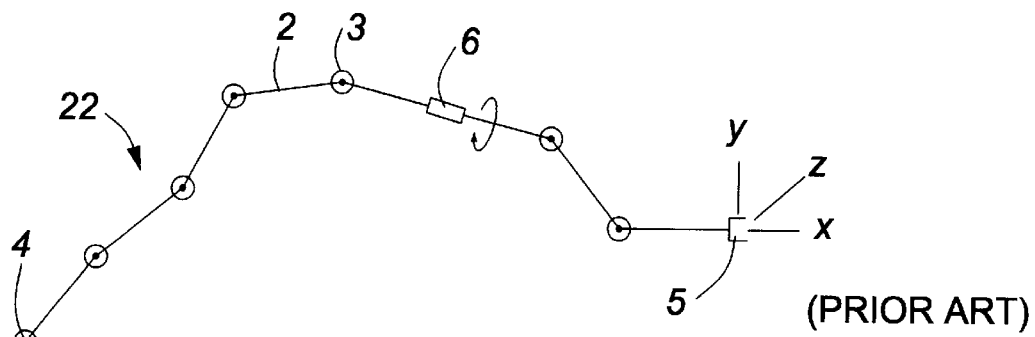
FIG. 2 is the mechanism of FIG. 1 with an additional rotary-twisting joint present.

FIG. 2 depicts a modified mechanism 22 to that of FIG. 1 that contains an additional "twist" joint 6 that also carries a sensor to indicate its rotational position. This twist joint 6 enables the end effector 5 to rotate out of the plane to which the mechanism 1 of FIG. 1 is confined, giving it access to a volume of three dimensional space.

Figure 3:
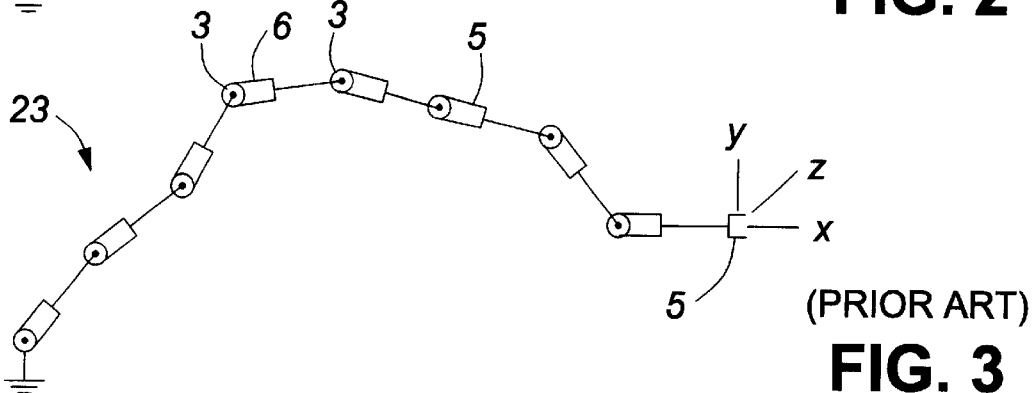
FIG. 3 is the mechanism of FIG. 1 with rotary twisting joints associated with each rotary-bending joint.
Figure 4:
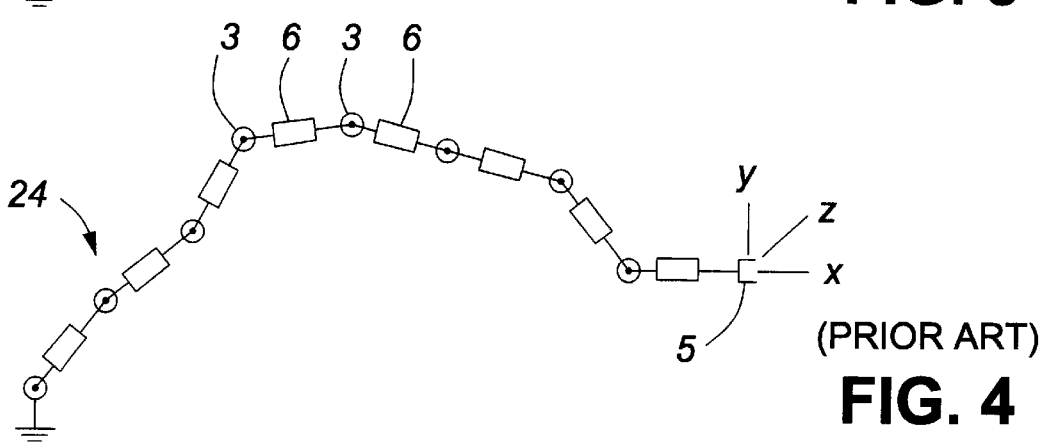
FIG. 4 is the mechanism of FIG. 3 with the twisting and bending joints separately disposed within the mechanism.

FIG. 3 shows a generalized expansion of the mechanism 22 of FIG. 2 wherein multiple twist joints 6 are provided, optionally shown co-located with bending joints 3, along the length of the modified mechanism 23. FIG. 4 shows a similar generalized expansion to provide a mechanism 24 wherein the bend 3 and twist 6 joints are distributed along the length of the mechanism 24 without necessarily being co-located.

The mechanisms of FIGS. 3 and 4 have the mechanical capability of conforming to some degree to a surface that is curved in three dimensions. However, with the use of rigid links and mechanical joints, such elements could not in the past be multiplied to provide a measuring tool with a high capacity for compliance with a curved surface.

Referring again to FIG. 1, it is possible to calculate the location in two dimensions of the end effector 5 and each joint 3 with respect to the reference point 4 using simple geometry based upon the length of each link 2 and the angular setting 26 of each joint 3. Similarly, such parameters can be calculated in three dimensional space for the mechanisms 22, 23, 24 of FIGS. 2, 3 and 4. To indicate this the symbols for x, y and z coordinates are provided opposite the end effector 5 in each of these Figures.

Figure 5:
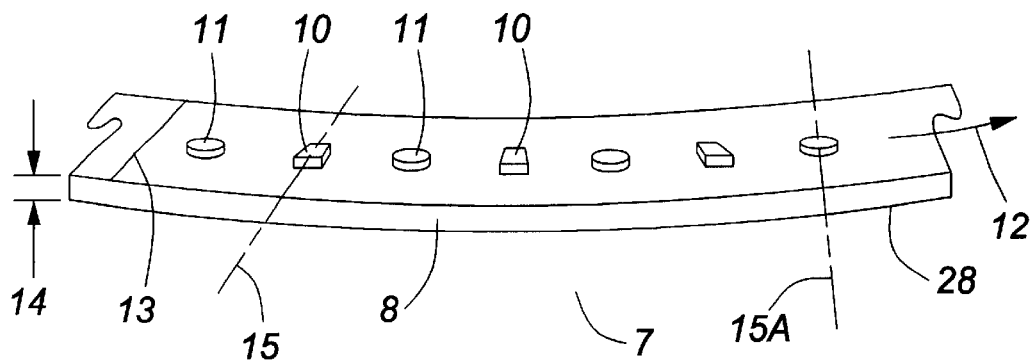
FIG. 5 is a pictorial depiction of a ribbon member in accordance with the earlier '672 patent, comprising a substrate carrying bend and twist sensors.
Figure 6:
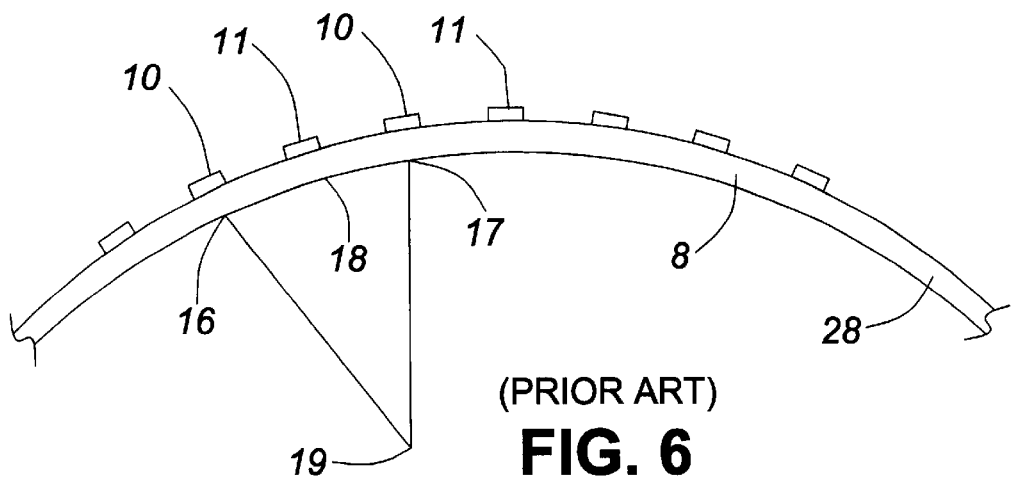
FIG. 6 is a side view of the ribbon of FIG. 5 bent into a curve.

FIGS. 5 and 6 represent embodiments of the invention of the aforesaid '672 patent, which carries this methodology into effect by providing, in one variant, a measurement member having a flexible ribbon-shaped substrate 8 to serve as a carrier for a series of flexure-detecting sensors 10, 11 distributed along its length. This substrate, as shown in FIGS. 5, 6 may have a reference surface 28 which may be applied against the outer surface of an object to extract a profile therefrom based on signals received from the sensors indicating their angular orientations.

This technique of measuring shape by sampling bend and twist using a flexible substrate 8 with a reference surface 28 can be applied if the bends and twists being measured are not permitted to take on sharp gradients, or if the sensor spacing is sufficiently small to adequately sample the gradients. The spacing and individual range of sensors determines the permissible range of operation for the sensor array.

In FIG. 5, and elsewhere herein, the term "ribbon" describes a body of flexible material that is essentially inextensible, has a longitudinal dimension 12 of considerable length compared to its width 13 and depth 14 and whose width 13 is so much greater than its depth that bending of the body is limited substantially to bending about axes 15, 15a which are transverse to the longitudinal dimension 12 of the ribbon and in the plane of the ribbon. A ribbon is, however, free to twist. For this reason the transverse bending axes 15, 15a are not necessarily parallel.

Figure 7:
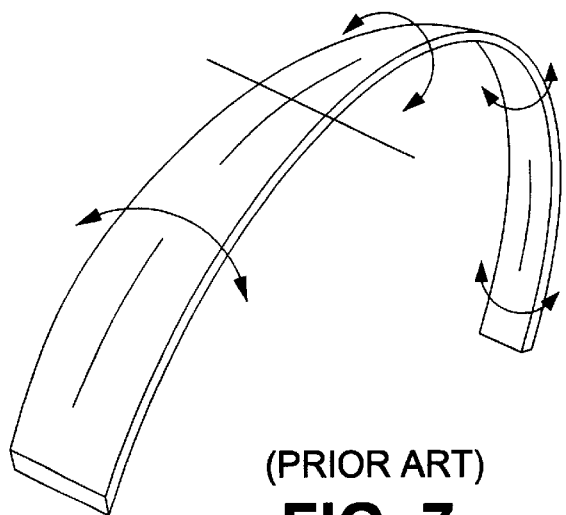
FIG. 7 is a pictorial depiction of a ribbon in space depicting bend and twist.

FIG. 7 depicts the ribbon substrate 8 with arrows indicating both bending and twisting.

In FIG. 5 the ribbon substrate 8 has distributed along and attached to its exposed surface 9a series of bend 10 and twist 11 sensors. These are schematically depicted as essentially point objects. In fact, all such sensors 10, 11 are coupled to a signal processing unit (not shown in FIG. 5) that receives signals from such sensors 10, 11.

In FIG. 6, the ribbon 8 of FIG. 5 is shown in a side view when bent within a single plane, without twist being present. The curvature between two points 16, 17 proximate to bend sensors 10 may be approximated as a circular arc 18 about a center 19. This approximation will be sufficient to provide reasonable accuracy if the ribbon 8 bends in a well-behaved manner e.g. if the ribbon 8 has relatively constant thickness 14 and flexing characteristic, and if the sensors 10 are sufficiently dense in their distribution along the substrate 8.

The curvature between points 16 and 17 can be estimated by the state of measured curvature at points 16, 17 as measured by the bend sensors 10, 10 located at those positions. If these curvatures differ, an average curvature, or a curvature value based upon further adjacent curvature measurements, may be taken as the approximated curvature for the arc 18.

Knowing the value of the curvature of the arc 18 and the arc length, being essentially the separation of the sensors 10 distributed along the ribbon 8, the position of a consecutive point 17 can be calculated with reference to an adjacent point 16. This type of inter-referencing calculation can proceed from a base end of a ribbon 8 to a terminal end. Such a calculation will provide geometric values for the positions of all of the sensors 10, 11 in space, plus by interpolation for any intermediate locations on the ribbon 8.

The above explanation has been made for simplicity by reference to the bend sensors 10 only. Similar calculations can incorporate data received from the twist sensors 11 to provide geometric data in three dimensional space.

If a flat untwisted section of substrate 8, of unit length, has two parallel ends, then twist is defined as the angular difference per unit length between the ends when a twist is applied. When the substrate 8 is also bent, the twist is interpreted to be the same as that present in, say, a thin cylindrical drive shaft along its long axis, i.e. the twist remains invariant as the shaft is bent. When this happens, the end lines are no longer in parallel planes.

If twist alone is applied to a straight section of the substrate 8, then the twist will not affect the position of the longitudinal axis line 12 until a section is reached which has a bend.

A model of the substrate's shape may be constructed in a computer, based on the above calculus. A convenient means of presenting the model visually is to draw the arcs in sequence, using small flat sub-arc segments, so that twist is also visible even for straight arc segments. Refinements may be added by use of interpolation, averaging, and other conventional curve fitting techniques.

Sensors suitable for bend and twist measurements on the substrates of the '672 patent include fiber optic bend and strain sensors; conductive elastomer sensors of bend and extension generally referred to as force sensitive resistors (FSRs), bend sensitive resistors (BSRs) and piezoresistive sensors; electrical strain gauges including bonded wire and semiconductor forms; and any other sensors capable of measuring bending, extension, and torsion, including capacitive, magnetic, and piezoelectric methods. However, the flexible member of the present invention relies on sensors which comprise portions of fibers which extend a good part of the length, and in many cases substantially the full length, of the member. These will usually be fiber optic bend sensors, or conductive sensors such as metal fibers, i.e. wires, which change their resistance under stress.

Fiber optic sensors such as those described in U.S. Pat. No. 5,321,257 and PCT publication WO 94/29671 (application PCT/94CA/00314), referred to above, are well suited for this application because these sensors are immune to electromagnetic interference and will function in the neutral axis of a flexure, where there is no elongation. The type of fiber optic sensors referred to in these publications can be classified as "Bend Enhanced Fibers".

Bend Enhanced Fiber sensors (BEF) are based on the loss of light from a light guide in a zone where the core/cladding interface has been treated and modified such that light striking the modified zone is lost from the core and does not return. In BEF sensors, a nominally straight fiber is usually treated on one side so that light loss increases as the light guide bends to make the straight treated zone more convex and decreases as the guide bends the other way. In some cases, the fiber is treated around a circumferential band so that bending in any direction in the region of the bend is detected. Sensors based on light intensity, as described, are attractive for low cost applications because signal processing can be very simple. However, intensity in a light guide can be a function of many things other than the measurand (curvature). Unwanted intensity modulators include:

Variations in optical connections

Bending of leads

Aging of light source

Aging of light guides

Effect of temperature on light sources and detectors.

One technique to reduce balancing requirements between fibers is to form a "lossy" zone, as by abrading or heating a local point in order to adjust the throughput of individual leads.

Looped fiber optic technology overcomes these obstacles by using an optical and electronic bridging technique involving two opposed laminated loops. This is fully described in the '672 patent with reference to FIGS. 23 to 26, and FIGS. 31 to 37.

Above, reference has been made to forming a tape or ribbon into a helix and monitoring or measuring the bends and twists in the helix. This and other forms of helix are particularly suited to members formed of the sensing fibers themselves, without any supporting substrate, and examples of such helical constructions will now be described.

A helix is defined rigorously as a mathematical space curve completely described by its bend and twist. The equation of the curve is:

$$R = r\sin(t)\mathbf{i} + r\cos(t)\mathbf{j} + bt\mathbf{k},$$

where the boldface i, j, and k are the Cartesian unit vectors for the x, y, and z axes, t is a parametric token, and R is the vector pointing from the origin of the axes to each point on the curve. r and b are described below. The first two terms describe the circle forming the base of the helix. The third term describes the 'rise' of the helix as it 'turns' around the base circle. The parameter t may be assigned a value of 0, in which case the first and last terms disappear, and the second term is r, described below as the base radius. If t is then assigned a value of 2 pi, the second term is zero, the first term is r, and the last term describes how far the helix rose during a complete revolution of 2 pi radians.

Figure 8:
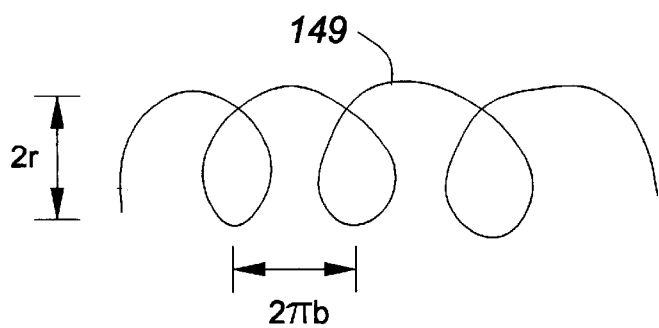
FIGS. 8 to 10 depict a helix and certain mathematical characteristics of the helix.
Figure 9:
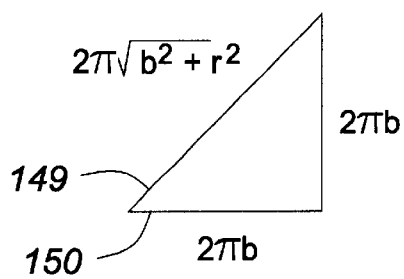
Figure 10:
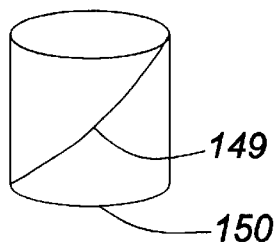

A two dimensional projection of a helix is shown in FIG. 8. The base of the space curve 149 has a diameter of twice the radius r, and a circumference of 2 pi times r. The pitch of the helix is defined as 2 pi times a factor b. The triangle 150 in FIG. 9 has an edge 149 with the length of a pitch, which is one complete cycle of the helix, or 2 pib. In FIG. 10 the triangle, which can be thought of as a triangular piece of paper, is bent into a cylinder so that edge 149 becomes a cycle of the helix.

Bend and twist of the helix are directly related to the r and b constants. Their derivation is available in most elementary mathematics texts:

$$\text{bend} = r/(r^2 + b^2)$$

$$\text{twist} = b/(r^2 + b^2),$$

where the carat notation, such as r^2, means 'r squared'.

A property of helixes is to transform an overall stress applied to the helix as a whole into a different type of stress in the coils of the helix. For example, tension applied to a helical spring results in a torque or twisting stress in the wire of the spring coils. Should a physical body in the form of a helix be bent by external forces (by this we mean that the centerline of the helix is bent), short sections of the helix will still be approximately helical, but will have different amounts of bend and twist than the parent, or unbent, helix. Should the helix be twisted about its axis, its bend and twist will be changed uniformly along the axis. An advantage of the helix is that bending and twisting tend to be distributed along the axis. This is advantageous when several helixes are twined together, as in a rope. Even though the rope has many fibers and strands, and few are on the neutral axis, it is capable of bending in two degrees of freedom and twisting in a third, with little likelihood of buckling or stress concentration.

In a rope or helical wrap, overall bending of the rope or wrap member is converted into repeating cycles of increased and decreased curvature along each fiber or strand of fibers, such that outward-facing curves of the fibers or strands have increased curvature, and inward-facing curves have decreased curvature. The net distension of any fiber due to overall bending is near zero.

Although there is an emphasis on helical forms in this disclosure, it is not meant to imply that cyclically repeating three dimensional forms are required to be strictly helical. Distended spirals (such as a spiral curve on the surface of a cone) also have many or all of the beneficial attributes of helixes, including smoothly varying bend and twist, and helixes in general will not be 'pure' if they result from wrapping a sensor about a human limb. Nevertheless, for simplicity, we emphasize helical forms for ease of demonstration of 3D versions of the invention.

Figure 11A:
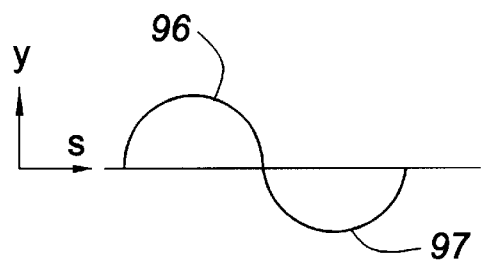
FIGS. 11a, 11b and 11c are graphs depicting the bending of the helix of FIG. 11.
Figure 11B:
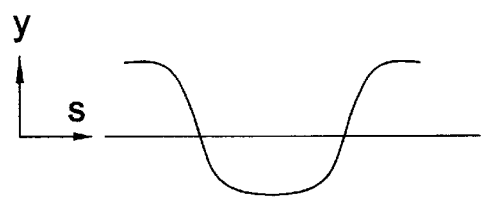
Figure 11:
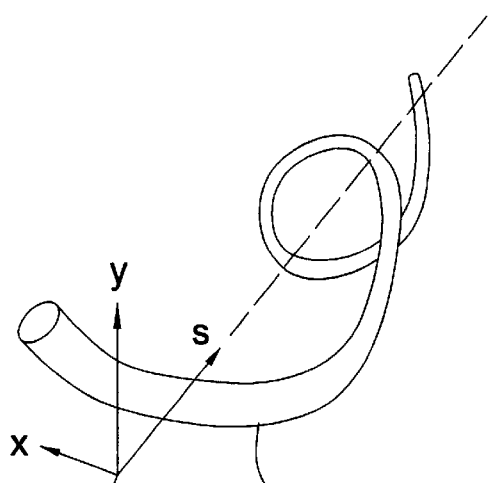
FIG. 11 is a perspective view of a helical fiber.
Figure 11C:
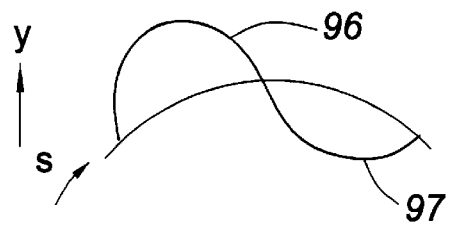

A helical fiber 90 is shown in FIG. 11. The triplet of arrows 92 indicates the centerline S along which the helix extends, and horizontal axis X and vertical axis Y. FIGS. 11a, 11b, and 11c show plots of the fiber locations along the S axis, which is straight for FIGS. 11a and b, but is that of a bent helix in FIG. 11c. FIGS. 11a and b show the sinusoidal nature of the locations for a single revolution of the helix. X and Y plots are 90 degrees out of phase. When the helix is bent in the SY plane, part of one cycle in Y takes on an increased downward curvature 96, while the other part takes on a decreased upward curvature 97. The plot of FIG. 11b describes the X dimension of the helix whether it is unbent or bent in the SY plane according to FIG. 11c.

The helical configuration is the basis for the construction of sensors like the rope sensor in FIG. 7 of the aforesaid '672 patent. In this case the rope may be provided with bend and twist sensors along its entire length, as described in this prior patent. The term "rope" as used herein can include merely several fibers twisted together so that the fibers are to some extent helical. Further description of how this can best be done is now provided.

Figure 12:
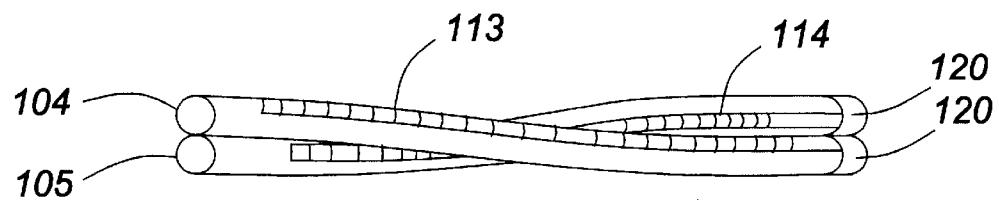
FIG. 12 is a side view of a simple rope type member in accordance with the present invention.

In FIG. 12 a very simple rope 100 is shown consisting of two optical fibers 104 and 105 twisted and bent around each other. Mirrors 120 are attached to one end, and couplers would be used at the other ends to allow injection of light and retrieval of reflected light. Mirrors can be formed by chemical or physical deposition of metals or by epoxies containing metal powder.

As with all ropes, the resulting entity takes on mechanical properties enhanced from those of each fiber alone (flexibility and distribution of stresses). The component fibers have, in effect, become a substrate with enhanced mechanical properties. The two fibers can be glued or otherwise held together at the ends to prevent unravelling. Whether or not the strands of the rope are physically connected, as by glue, the fact that the fibers are in contact with each other along much of the length of the rope means that they are in mutually supporting relationship and have greater strength and integrity than a mere bundle of fibers.

Proven rope construction methods are applicable to sensory rope as well. For example, strands of fibers, including optical fibers, may be counter-twisted when twined together to form a rope, which tends to maintain the integrity and form of the rope. Bends and twists applied to the rope are transferred to the fibers themselves and can be sensed by sensors forming parts of the fibers, if we use optical fibers which have been treated to become bend sensitive as described above. Treatments can take the form of loss zones applied along the axial extent of the surface of each fiber, such as loss zones shown as hatched areas 113 and 114 in FIG. 12.

Figure 13:
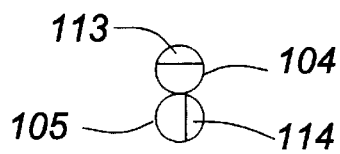
FIG. 13 is a cross-sectional view of the rope of FIG. 12.

A cross section of the two-fiber rope is shown in FIG. 13. The loss zones 113 and 114 at selected sides of the fibers are shown with an orthogonal arrangement, such that one loss zone faces vertically and the other faces horizontally. The orientation of the zones need not be exactly orthogonal, since the sensors may be calibrated by applying bends in known planes. The characterizations in each plane can be used to solve two simultaneous equations to find two unknowns: the bends in orthogonal planes, or 'x and y' bends. Twist requires another fiber and a pose or poses including known twist. In general, any rope-like flexure has three degrees of freedom described in the '672 patent as two degrees of bend freedom and one of twist. Thus, three equations are required to solve for three unknowns. This implies three sensors for fully determining the flexure at one position along the rope.

Figure 14:
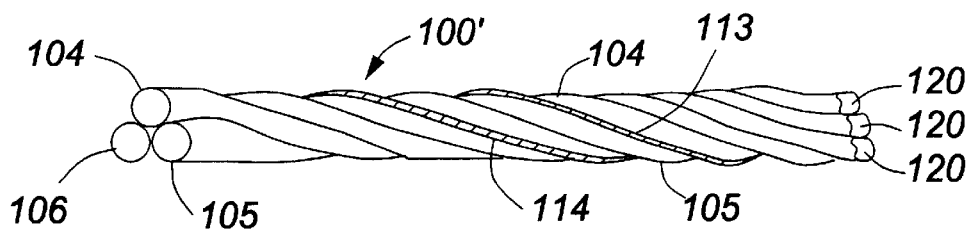
FIG. 14 is a side view of another rope type member in accordance with the present invention.
Figure 15:
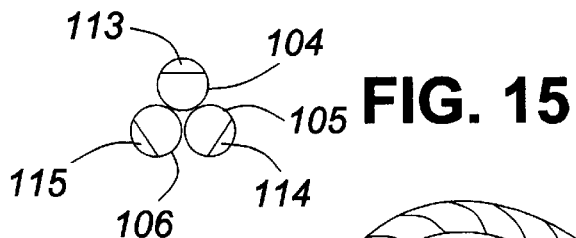
FIG. 15 is a cross-sectional side view of the rope of FIG. 14.
Figure 16:
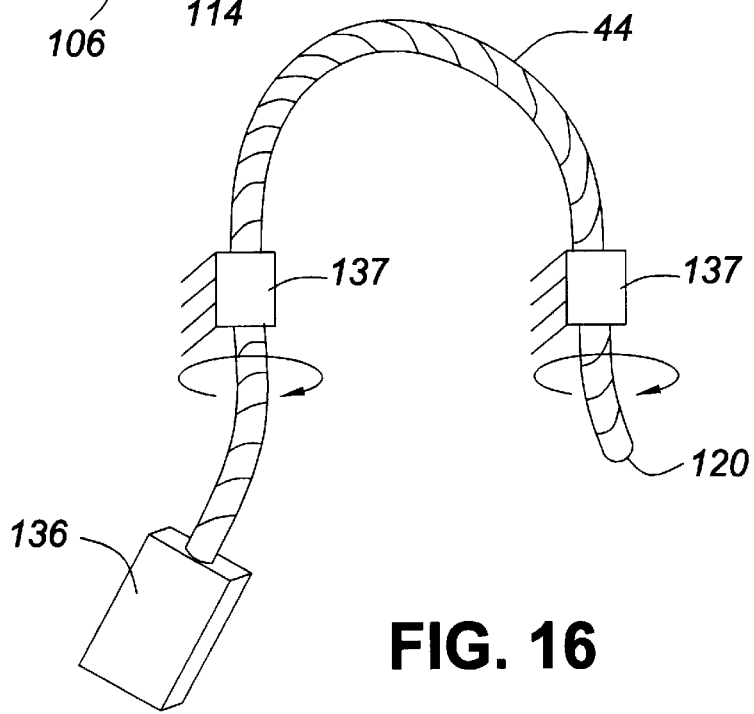
FIG. 16 is a view of calibrating equipment for a rope member such as that of FIG. 14.

A three fiber arrangement is shown as rope 100' in FIG. 14. Two of the treated bend sensing zones are again shown as zones 113 and 114 on fibers 104 and 105. Mirrors 120 are also shown. The third zone is hidden by the rope, but this zone 115 is shown in FIG. 15, a cross section through the rope within the region that has been treated. The zones 113, 114, and 115 of FIG. 15 are shown as being at approximately 120 degrees separation from each other circumferentially around the rope. The separation is optimum for solving for 2-axis bend and twist, but need not be exactly 120 degrees. One need only avoid angles that significantly degrade accuracy. For example, if two sensors both face in the same direction, they contain the same information, so that a solution for three degrees of freedom is not possible. Similarly, sensors that give nearly the same information are of little use. Solution for bend and twist involves forming three equations in three unknowns, of the form:

(eqs 100–103):

$$\text{sensor\_output\_1} = \text{bendcal\_1} * \text{bend\_1} + \text{twistcal\_1} * \text{twist};$$

$$\text{sensor\_output\_2} = \text{bendcal\_1} * \text{bend\_2} + \text{twistcal\_2} * \text{twist};$$

$$\text{sensor\_output\_3} = \text{bendcal\_1} * \text{bend\_3} + \text{twistcal\_3} * \text{twist};$$

where bendcal and twistcal are the bend and twist calibration constants from placing the rope in known bend and twist poses. Convenient bend poses are semicircular, in orthogonal planes. Twist can be applied to a straight rope. Both can be applied using a fixture as shown in FIG. 16. Bearings 137 attached to the same reference frame at their outer circumference hold the rope 99 at both ends. The rope is bent into a semicircular shape. The bearings may be rotated synchronously to apply continuously varying bend to each sensor in the rope, because each sensor will face out at different angles as the rope rotates. A phase difference between the two ends can be used to also apply known twist. The optoelectronic interface box 136 must be fixtured to allow it to rotate, as must any attachments at the other end, such as the mirrors 120. The output of each sensor on the rope, when used in the calibration fixture of FIG. 16 rotating at a constant rate, is a sine wave. The sine waves vary in phase according to the circumferential facing angle of each sensor. If twist is added by creating a mechanical angular offset between the two rotating bearings, but they are still rotated at a constant rate, the facing angles will take on new phase angles relative to each other, proportional to the twist.

In the above discussion of calibration, we have assumed that each sensor output can be associated with the location of a sensor in the rope. The association may be known before the calibration operation, by knowing the organization of the fibers within the rope and the connection of each fiber to each readout device (e.g. optical emitters and detectors). However, the association may also be made during calibration, by imposing shapes on the rope that provide axial and circumferential geometry references. For example, while the rope is rotating in the the above calibration fixture, its overall form may be indented locally such as by a smooth rod held orthogonally to the axis of the rope, pushing down on the arch of the rope. The local indentation will affect a subset of sensors in a major way at that axial location, producing an excess bend in the subset. The subset will normally comprise three sensors with circumferential orientations at approximately 120 degree intervals. The phase of the outputs of these sensors will indicate their circumferential orientation relative to any chosen reference sensor along the rope (normally at one end of the rope). The fibers being affected can be identified by these outputs, associating such fibers with the sensing locales that are being activated.

Alternative methods involve holding the rope between formed plates, looping it around a rod and moving the rod and loop down the length of the rope, or even vibrating the rope with known standing wave patterns or known dynamic twists and turns (as in swinging a lasso in a controlled way). It is also possible to determine the association using quasi-random mechanical inputs and associative software such as a neural network.

In fact both associations and locations for all sensors in a rope that has been assembled with a random or quasi-random axial or circumferential placement of sensors may be determined using the above calibration techniques, since the techniques reveal both axial and circumferential information and connection for all sensors. Normally, this would be done for ropes that have been built with redundant sensors to compensate for sensors that are found on calibration to have the same or very similar circumferential orientation. Fortunately, it is possible to construct ropes so that the sensors have known orientations, even if the loss zones of the sensors are very long. This can be explained by referring to the helix equations. Twist is $b/(r^2+b^2)$. If r is small compared to b (true for practical ropes), then twist is approximately $1/b$. Over the pitch length of the fiber (2 pib), the center of the fiber will have a mathematical twist of $1/b$. This is equivalent to a twist of 2 pi over one pitch (one complete turn of the helix). The pitch length for practical ropes made from 0.25 mm diameter fibers is approximately 1.5 cm. Because of their torsional stiffness, plastic or glass fibers easily resist taking on a twist of 2 pi per 1.5 cm, so it is easy to build a rope that has a mathematical twist at the centerline of each fiber of 2 pi per pitch, yet a torsion of zero, simply by winding the rope and allowing the fibers to untwist whilst so doing. This means that a fiber can be pre-treated with a straight axial loss zone, then wound into a rope, and the loss zone will remain facing out from the rope in the same direction along its axial extent. The lost light can be thought of as emanating in or nearly in a plane. By pre-rotating the fibers circumferentially before winding a rope, the planes can be arranged at 120 degree separations or any other desired angular separations. It is simple to confirm these assertions by winding large wires marked with axial lines into rope forms. Unless pains are taken to apply twist and maintain it by binding the fibers together tightly, the axial lines will face in constant directions along their lengths.

Long axial treatments for bend sensitivity are necessary to achieving distributed sensing, which determines net angular curvature over a sensor length even if the sensor is not uniformly bent or twisted. As described in the prior art patents referred to above, the treatment may be piecewise continuous, since the bend and twist fields tend to vary slowly over the axial length. Distributed sensors tend to minimize errors from bend or twist variations within a sensor length, since angular heading of each portion of the rope or ribbon is maintained. However, it is also possible to allow twist to build over a fiber length, or to purposely apply extra twist to each fiber when winding the rope, as is done in some ropes and cables. This has the effect of twisting a long sensitized zone so that it faces out from the rope at varying angles along the axial extent of the rope. In the extreme, this prevents sensing of bend, since the sensor becomes circularly symmetrical at every pitch length. However, if the treatment is periodic along the fiber, at the same frequency after winding as the pitch, it can still function as a pure bend sensor. The periodic zones can be fairly long, as long as they do not occupy more than 180 degrees of the circumference, and can even occupy more, but with reduced sensitivity to bending. It is also possible to treat fibers after winding, in continuous or piecewise continuous fashion.

Figure 17:
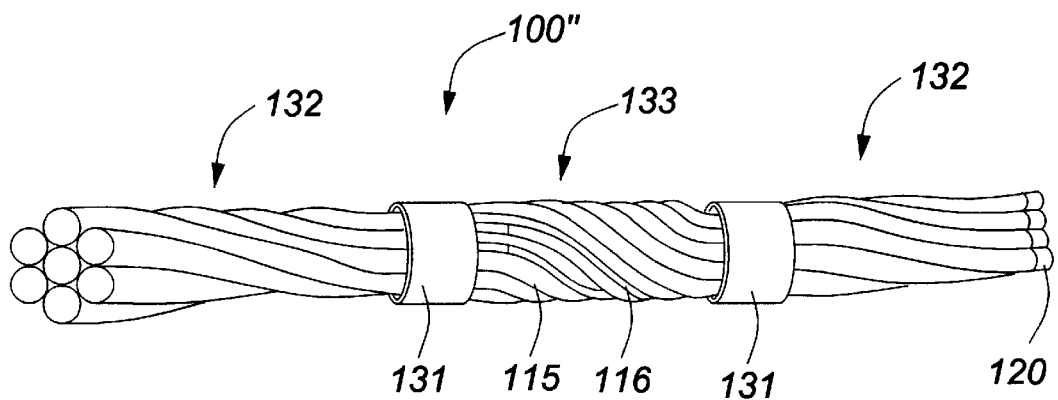
FIG. 17 is a view of another rope type member, this having enhanced twist sensitivity.

Twist sensitivity of rope constructions is fairly small and is not always monotonic for both directions of twist (clockwise and counterclockwise). Nevertheless twist sensors can be used to find shape over restricted ranges. Twist causes rotations of the fibers about their axes, which exposes the loss zones to different curvatures; and to increased bending of the fibers as the rope 'winds up'. Enhanced twist sensing useable over any practical range of shapes for the rope is achieved by winding the rope to achieve a tighter construction with more bend and twist. This produces a monotonic response to twisting, because the rope fibers never separate during untwisting, which can cause lack of predictable or sizeable response. By 'monotonic' or 'bipolar', we mean that the light throughput increases for one direction of applied twist and decreases for the other. The twist sensitivity in this pre-twisted zone is much larger (more than 10 times larger) than for the surrounding fibers that were not pre-twisted. The primary cause of twist sensitivity is not fiber treatment, but rather microbending of the fibers at tight radii during twisting. The enhanced sensitivity can be placed at a selected location along the rope by adding more twist to a section and then preserving it by clamping the edges of the section. This is shown in FIG. 17, where a rope 100" has regions of low constructed twist 132, and a region of high constructed twist 133 maintained by constricting bands or adhesive 131. Alternatively, the region may be twisted sufficiently that it maintains the pre-twist without adhesives. This is possible in plastic materials like polymethylmethacrylate fibers. They may be twisted slightly beyond yield, tending to maintain the pre-twist, or friction alone will tend to maintain the pre-twist. Mild heating also helps to set the form of the twist-sensing region in plastic fibers. Even glass fibers may be pre-twisted, although heat and re-cladding may be required. Glass fibers may be so heat treated by pre-twisting in a rope or 'yarn' at high temperature, then unravelling to re-clad, then twining into a rope again. All such fibers will maintain their non-straight form by reason of pre-twisting with heat treatment or other processes indicated above which produce permanent deformation of the fibers.

Sensor treatments 115 and 116 are shown within the pre-twisted section. Because twists and bends change gradually over length, the bend sensors could also be distal or proximal, or both, with respect to the twist sensing section. It is also possible to place bend sensors in another rope, and to twine the twist ropes and bend ropes together, so that the two ropes are really strands of a parent rope. Normally, the bend and twist treatments would be arranged on their strands at the same axial location along the parent rope.

The method of twist sensing shown in FIG. 17 leads to a slightly different form of the bend and twist equations 100–103 (above), if the twist region is used on the same fibers that are treated to sense bending. The twist signals are still additive, but the twist zone also responds to absolute value of bending, producing a decrease in light throughput for all fibers in that strand, for any bend along any axis. The bend response is circularly symmetrical. This results in common twist and common absolute value of bend terms in the three equations. Nevertheless, there is still a solution for the three unknowns, based on known calibration constants. The twist zone, plus two bend treatments, are sufficient. If the twist zone is separated onto a different strand, then there is also a unique solution to the equations, and less interaction of the terms.

In a preferred embodiment, pure bipolar twist sensing may be provided, without any sensitivity to bend. A pure twist sensor may be formed by the pre-twisting described above, if the twisted fibers are few in number (usually two twisted together) and are, after pre-twisting in a region, wound into a strand with other fibers that have not received any pre-twisting. A particularly useful aspect of cyclical structures is exploited. In FIGS. 11, 11*a,* 11*b,* and 11*c* it was shown that a helical fiber takes on uneven amounts of curvature as shown at 96 and 97 in the Y vs. S plot of FIG. 11*c.* Its curvature in the X dimension is unaffected, as shown in FIG. 11*b.* Because there is some mechanical interaction of the fiber with its mate in the twisted pair, and the light is distributed toward the peripheral aspect of the fiber circumference, there is some net signal change even though the curvature increase of the '96' half of the cycle is theoretically equal and opposite to the curvature decrease of the '97' half of the cycle. Without the second-order effects, the sensor would already be a 'pure-twist' sensor, but instead it does respond in non-bipolar style to applied bends. This aspect is eliminated when it is wound into another, larger strand, or wound around a larger cylindrical core. It then follows the bend of the core or strand in the same horizontal and vertical shapes described by FIGS. 11*b* and *c,* but at a larger scale. At that scale, the secondary effects disappear, and with them the bend sensitivity. There is no diminution of twist sensitivity. Because it is operating at a larger scale, the theoretical nulling of the bend increase and decrease of FIG. 11*c* is achieved.

The above discussion raises the question of how a bipolar sensor treatment can detect any bend on a helix, if the net bend in the 'Y' plane of the example is zero, and the bend in the 'X' plane is unchanged. However, a bipolar sensor on a 'zero-twist' fiber always faces in the same planar direction anywhere along a helix. If that plane is aligned with the YS plane, the sensor signal will decrease in the '96' half of the cycle due to increased downward bending, and will also decrease in the '97' half of the cycle due to decreased upward bending. So, there is no contradiction that a fiber 'treated' to have circularly symmetrical sensitivity to bending will detect no bend in a helix, yet a fiber that has bipolar sensitivity will detect bend in a helix. Thus, a useful pure-twist sensor may be formed by simply pre-twisting fibers in a location and placing these in a larger helix.

Another desirable method to form a 'pure-twist' sensor is to create a region of increased twist as shown in FIG. 17, that occupies a full turn, or multiples of full turns of the helix occupied by a fiber. Twist will be sensed but bend around any axis will cancel along each helix.

Figure 18:
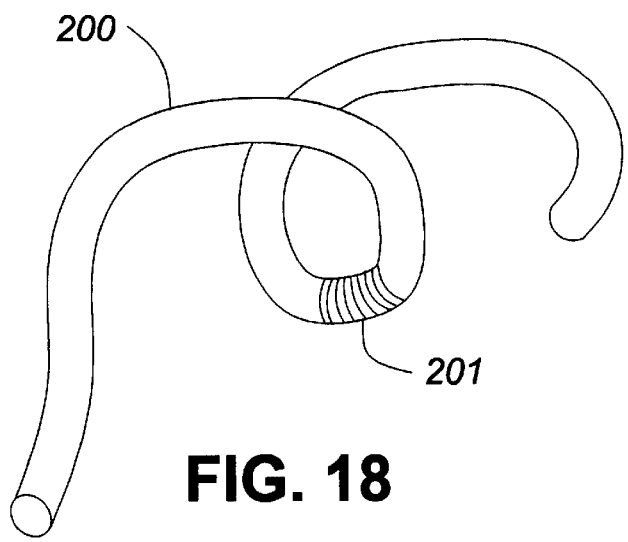
FIG. 18 is a perspective view of a sensing fiber which may be used in the rope of FIG. 17.
Figure 19:
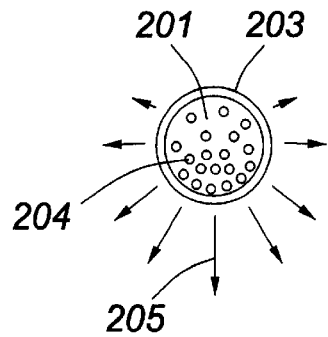
FIG. 19 is a cross-sectional view of the bend sensing portion of the same fiber.

FIG. 18 shows one fiber 200 of a helical rope, or strand of a rope. A circularly symmetrical treated region 201 allows light to escape over a short portion of a helical turn. A section through the fiber at loss region 201 is shown in FIG. 19. The circular band 203 surrounding the fiber represents a purposely induced loss region made by abrasion, etching, or the like. It allows light in the core 201 to escape wherever it impinges on the circumference. Light flux in the fiber is shown as small circles 204. It is always most dense at the outward-most portion of the turning fiber, which faces downward in the figure. Thus, the circles 204 are drawn with greatest density near the bottom of the fiber. The arrows 205 surrounding the fiber indicate by their length the increasing light loss toward the bottom of the fiber. Thus, the bend of the helix transforms the circularly symmetrical treatment into a bend sensor with a loss that is directed mainly toward a specific circumferential angle. This permits simple manufacture using symmetrical etching or abrasion techniques, yet can be used to produce sensor triads by varying the axial placement of three such regions on three fibers in a rope. If the regions are extended axially to each occupy a full turn of the helix, symmetry is again achieved, and the triad becomes a twist-sensing region.

Figure 20:
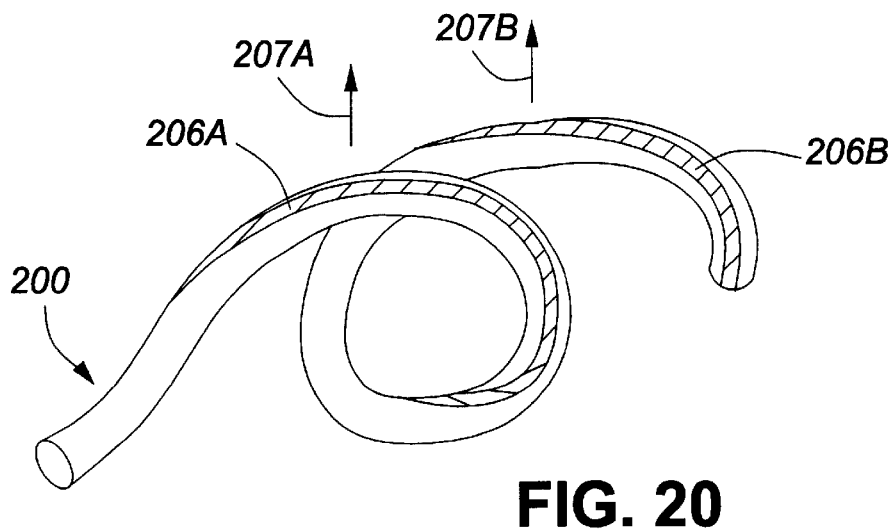
FIG. 20 is a view similar to FIG. 18 of another sensing fiber.

FIG. 20 shows another example of a treatment that exploits the bend and twist pre-existing in any helix. FIG. 20 shows optical fiber 200 in a helical form, typical of a fiber in a rope. In this case the fiber is treated in a narrow axial band 206 that was straight before the fiber was wound into the rope. When wound into the rope, the fiber was twisted so that the band now cycles around the circumference of the fiber in a 'band helix' on the 'fiber helix'. The band helix appears at the outward-most portion of the fiber helix only once per revolution of the fiber helix. It appears at location 206A, the start of a turn, and 206B, taken to be the start of the next turn. Because light interacts with the loss zone maximally at 206A and 206B, arrows 207A and 207B are drawn to indicate the preferred axis of the resulting sensor. Other portions of the treatment 206 also lose light, but less so, according to a cosine law describing the circumferential angle of the treatment, interacting with the light flux, which is always maximal toward the outside of the helix. This produces a sensor that senses bend with a bipolar response to bending of the helix along a chosen circumferential angle of the helix, even when the loss zone is a full turn long, or even longer. If a twist of less than one turn per pitch is applied to the fiber during building, and a continuous (or piecewise continuous) narrow axial treatment extends for more than one turn of the helix, a bend sensor with a spatial distribution of more than one pitch length can be made. If a large 'build'-twist is applied, a combined monopolar bend and bipolar twist sensor can be produced. The twist sensitivity results from the treatment band appearing so frequently at the outward-facing angle that bipolarity is cancelled. The sensitivity when build-twist is large, is similar in nature (monopolar in bend, bipolar in twist) to that of untreated fibers that have been build-twisted, only it may have a larger magnitude of response. Such treatments may be associated with other regions that have bipolar sensitivity to bend, to resolve the 3D state of the bend and twist of the helix exactly.

In an alternative embodiment, a twist sensor may be formed by twisting one fiber about another straight fiber, so that the first fiber describes a helix about the second straight fiber. The helical fiber will attenuate light throughput when twisted to decrease the radius of its bends, and will attenuate less when twisted the other way. The straight fiber is not necessary to this performance and may be removed. There is no response or very diminished response of this embodiment to bending.

The build-twist can be applied to a single fiber in a strand or rope, to multiple fibers, or to all the fibers, producing single or grouped twist and bend sensing in a desired axial location. When the treatment and build-twisting cover more than one pitch length of the helix, two main sensor types can result. If the build-twisting produces a band helix that repeats at the same spatial period along the fiber helix as do the turns of the fiber helix, a bipolar bend sensor is produced, with its plane of sensitivity passing through the outer-most facings of the treatment band. If the period of the band helix repeats at a higher frequency, monopolar response to bend will tend to result, accompanied by bipolar twist sensitivity. The preferred embodiment is a pure-twist sensor formed by pre-twisting two fibers in a region, then winding the pair into a strand with other fibers, or winding it around a central core (endoscope, tubing, etc.) along with bend-sensitive fibers.

Figure 21:
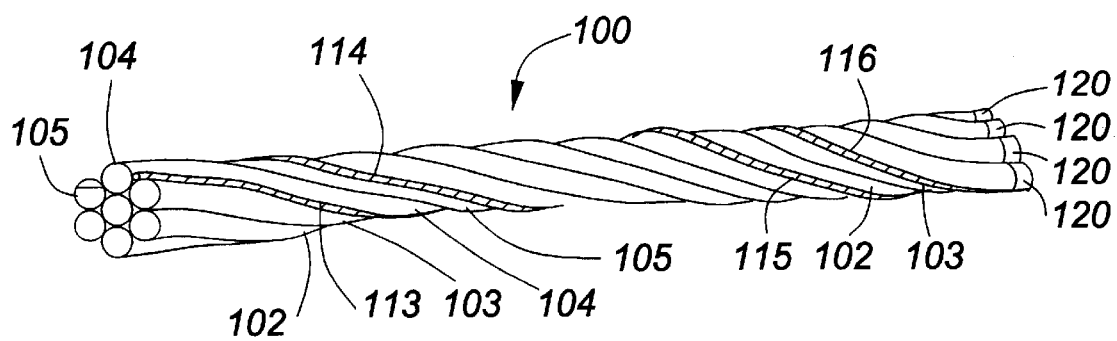
FIG. 21 is a side view of yet another rope type sensor.
Figure 22:
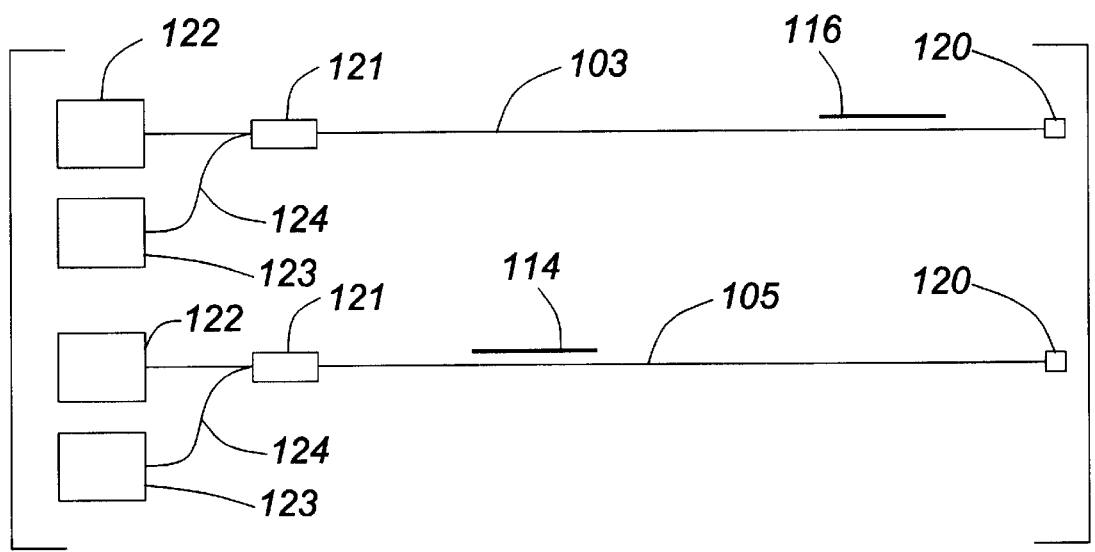
FIG. 22 is a diagrammatic view of sensing optical fibers connected to their optical circuit.
Figure 23:
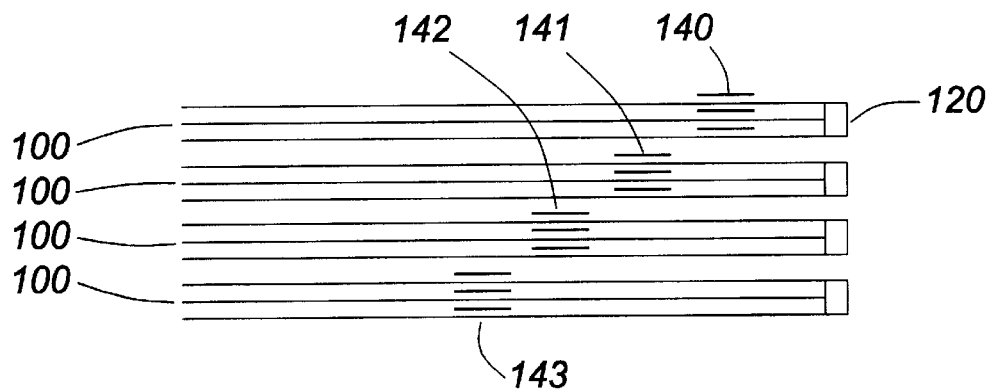
FIG. 23 is a diagrammatic view of the component fibers of a rope showing the positions of their sensing portions.

So far, we have described sensor pairs and triads that determine bend and twist at only one location along a rope. However, members in accordance with this invention, as in the aforesaid '672 patent, will normally be required to measure bend and twist at more than one location along the member. This can be done by forming arrays of pairs or triads along a rope. An example is shown in FIG. 21, where fibers 102, 103; 104, and 105 are shown with treatment zones 115, 116; and 113, 114 respectively. Mirrors 120 are affixed to the distal ends. The optical circuitry is shown in FIG. 22 for fibers 103 and 105. Their loss zones, 116 and 114, are at different axial locations, on fibers shown straight for convenience of drawing only. Light sources 122 send light through directional couplers 121, through the sensors 116 or 114, to be reflected from mirrors 120, back through the sensors, to exit the directional couplers in their lower fiber legs 124 and enter the photo detectors 123. A more complete system for a rope, again shown with straight fibers for convenience, is shown in FIG. 23. Strands 100 each consist of three fibers, with a triad of sensor regions on each strand. The four triads are marked 140, 141, 142, and 143. Mirrors 120 are placed at the ends, one mirror per fiber (the figure groups three mirrors into one block for drawing convenience or the block can refer to a common reflective fitting described below).

While it will be normal for a member in accordance with this invention to have one fiber for each bend or twist sensor, as indicated in FIG. 23, it is possible to use light absorbing surfaces on the fibers which are selective to specific wavelengths of light, and photo detectors which also discriminate between different wavelengths, and in this way use one fiber for several spaced apart sensors.

FIG. 24 shows an alternative looped configuration for a sensing strand. Three fibers have tight loops, so that six 'runs' of fiber from three loops 130 are wrapped around a central core fiber 107. The loops are conveniently placed at slightly different axial extents, so that they nest. A leg (or, if desired, both legs) of each loop may be treated before the rope is formed. This can be done on a flat surface with the treatments in a plane parallel to the surface, as described above. The loop maintains orientation of the treated section during construction. The loops may be placed in a star pattern at the end of the rope. This will automatically place the treatments at angles facing approximately 120 degrees apart if the rope is wound with zero twist. It also results in a 'star' pattern for the fiber ends at the left side of the figure: fibers 104A and 104B belong to the same loop. Similarly, fibers 105A and 105B, and 106A and 106B belong to the other two loops respectively.

The treatment on the fibers of FIG. 24 may be near or directly on the reversing loops, or distant from them. According to the prior art including PCT/CA94/00314, placement near reversing loops results in synergy between the geometry of the reversing loops and the loss zones that results in an enhanced sensing of bending. According to the same prior art, the synergy also results from treatment within any curved portion of a curved fiber in general, without requiring that the curved portion be a reversing curve. A sinuous or helical form provides a multiplicity of sites that may be used to both enhance sensitivity to bending and to plan the orientation and axial placement of such sites within the overall design of the sensing array or member.

The 'six on one' construction (six fibers surrounding a single core fiber) is a familiar one for conventional mechanical ropes, as are the triple fibers of FIGS. 24 and 25. For sensory ropes, the central core fiber is often left as a mechanical-only component, but it can also be used as a sensory element or as a common illuminator or return fiber if a mirror is also used. In no case is the central fiber, if used at all, essential to the functioning of the sensory rope. The rope has sufficient mechanical integrity without the minor addition of stiffness from the central fiber. Rather, it simply aids in the forming of the rope and fills a central void during flexing. This is quite different from the role played by a central substrate holding mechanically subservient sensory fibers described in the '672 patent.

Mirrored construction is shown in FIG. 25, where a section through part of the end of a strand 399, of fibers 401, 402, 403 (and three others not shown) surround core fiber 400. A small cap 404 is attached to the circumference of the cut fiber ends. The cap includes an inner concave mirrored surface 405 that serves to return light 407 exiting the fibers to the central return fiber. The return light is shown by arrows 408. The light may also be directed the other way. In the former case the circumferential fibers are multiplexed in time or wavelength-encoded to provide for their separate detection after collection in the central fiber. In the latter case, the central fiber provides steady illumination and separate light detectors are used on the circumferential fibers to generate signals unique to each fiber. FIG. 26 shows a section through 409–410 of FIG. 25.

It is also possible to use strands of sensory fibers on the outside of a core. In this embodiment, the fibers shown in FIG. 27 would be replaced by strands comprised of fibers, or ropes comprised of strands of fibers. The covering fibers of FIG. 27 could also be woven into a cylindrical covering, by intertwining fibers from successive layers. It is also possible to form the structure of FIG. 27 by winding a 'ribbon cable' of fibers as a helical wrap about a central core. In this variation, it is best to use a ribbon cable held together by a loose carrier of thread, or for the structure itself to hold the ribbons together, so that the constituent fibers may slide by each other during wrapping. Otherwise the method is only suitable on very large forms.

In 'core-surround' cases covered by this patent, the core plays a mechanically subservient or synergistic role to the fibers, providing in substance a means of sustaining the outer covering in a circular cross sectional form during bending and twisting. As an example, the core in FIG. 27 may be removed and the fibers will maintain their circular cross sectional form during minor bending. Similarly, the core alone will be able to flex to some degree without buckling without the aid of the fibers. However, the core and fibers combined are able to maintain a circular cross section during more extreme bending, and the fibers impart significantly enhanced resistance to twisting of the core because their circular cross section is maintained. The core and fibers mutually prevent buckling in bend or twist that would occur in either without the synergistic construction.

In all forms of rope it is possible to add a surrounding layer of non-sensory fibers to protect the underlying sensory fibers. The surrounding layer is preferably helical, woven or knit, so that it will conform to shapes in a manner similar to that of the underlying layers.

The large core 107 of rope 100 may be a solid fiber or rod, or could be hollow. The surrounding fibers, such as 104 and 105, end in mirrors 120 or could be looped. The loops could return through the hollow core, or a hollow core could contain an endoscope, catheter, or fluid path. It is also possible to add other layers above the ring of fibers shown. Layers can be wound alternately clockwise and counter-clockwise to increase strength and reduce unravelling tendencies. This is also a means of increasing the twist modulus, to reduce the ability of the sensory construction to twist about its axis.

Figure 28:
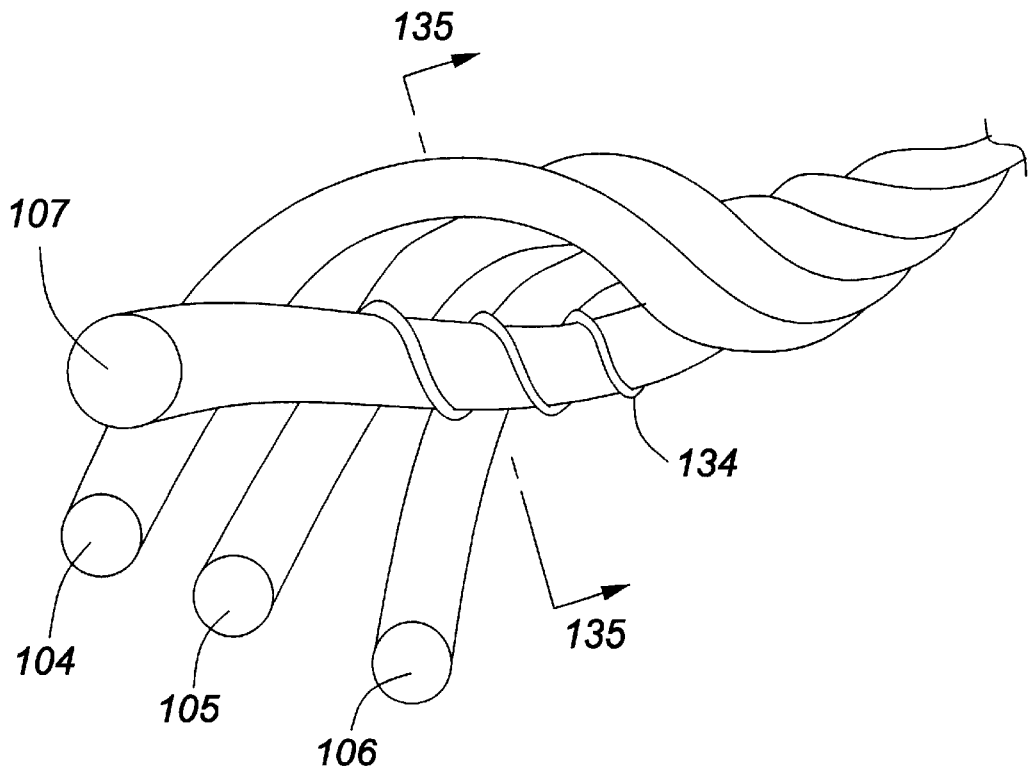
FIG. 28 shows a perspective view of parts of a rope also having a core.
Figure 29:
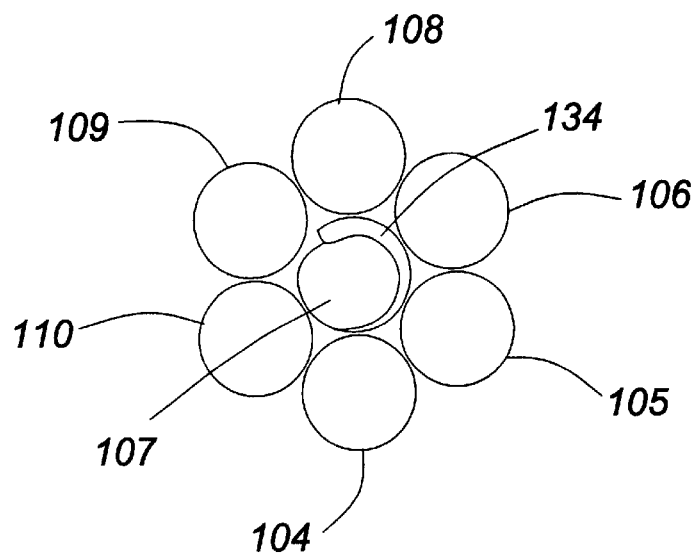
FIG. 29 shows a cross-section through the rope of FIG. 28.

An alternative bend and twist sensing means is shown in FIG. 28. A small wire or fiber 134 is wound around the central core fiber 107. Fibers 104, 105, and 106 are shown surrounding the core in a helical wrap. The wrap is opened up and other fibers are removed from the drawing, to reveal the extra wrapping 134. All the fibers 104–110 and a portion of the helical wrap of wire or fiber 134 are shown in FIG. 29, a section through 135–135 of FIG. 28. The extra wrapping is designed to create microbending losses in the surrounding fibers when the rope is bent. The losses will be maximal on the outward side of the bent rope, in the plane of the bend, because on that side the fibers press maximally on the extra wrapping 134. Similarly, twist will cause an overall decrease in the light transmission of all the fibers. If six fibers surround the core 107, then six equations in three unknowns can be formed and solved for 2-axis bend and twist.

Figure 28A:
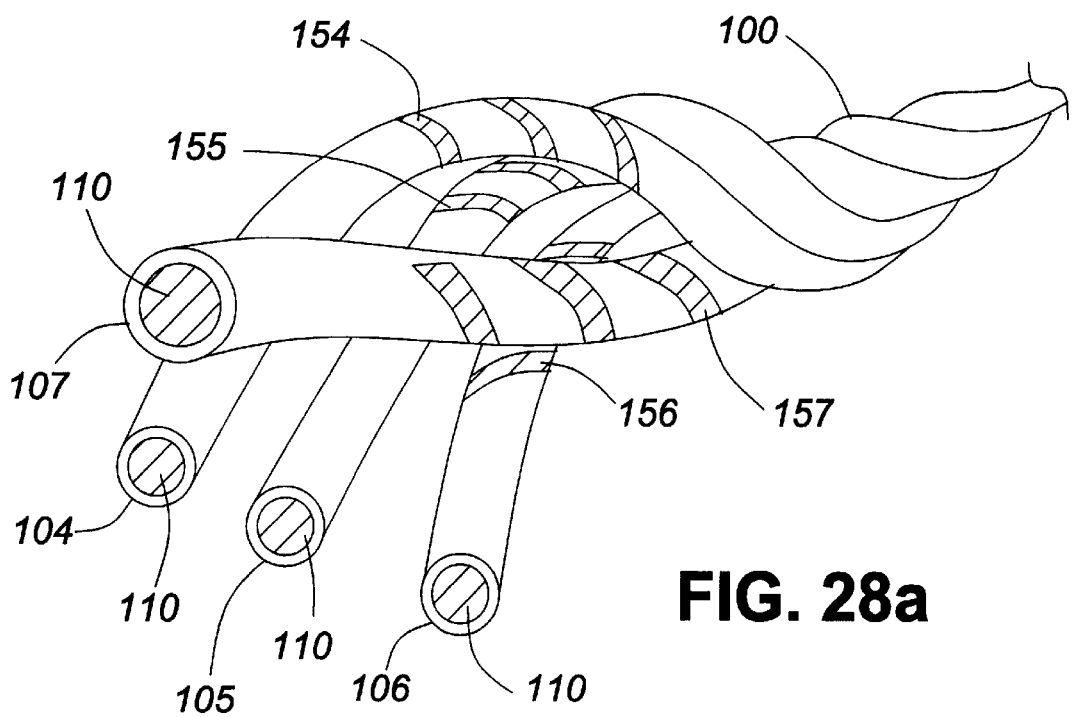
FIG. 28a shows a rope form of the invention which relies on capacitance sensing.

An alternate construction using capacitance sensing is shown in FIG. 28*a*. As in FIG. 28, only three fibers 104, 105, and 106 of a larger set are shown surrounding central fiber and these fibers are shown partly unwound to reveal the sensing structures 107. In this alternate construction, the fibers are coaxial electrical conductors each having a helical sensing 'groove' 154, 155, 156, and 157 where the coaxial shielding has been modified to permit capacitive coupling between inner conductors 110 of the surrounding fibers and inner conductor 110 of the central fiber 107. The sensor is based on varying the coupling according to 3D bend and twist of the 'capacitive rope'.

The capacitive rope sensor employs to advantage the differential bending within each wave of a helix, shown previously in FIG. 11*c* as a half wave with increased bend 96, and a half wave with diminished bend 97, with no net distension of the fiber. When a rope is bent, portions of fibers in the plane of the bend will respond with large differential bends 96 and 97, and portions orthogonal to the bend will experience no differential bends (as shown in FIG. 11*b*). In between these orthogonal extremes, the differential bending varies as a cosine of the circumferential orientation. This gives rise to relative slippage between adjacent surrounding fibers, and between a surrounding fiber and the central fiber 107. The slippage varies with axial position along the fibers and with circumferential orientation around the central fiber.

The pitch and width of the coupling grooves 154, 155, 156, and 157 may be chosen so that coupling between a surrounding fiber and the central fiber varies maximally for bends in a given plane. This will happen, for instance, if the surrounding coupling grooves 154–156 have nearly the same axial placement, varied only slightly to ensure grooves on surrounding fibers register with the groove on the central fiber at their locations of closest proximity. This requires only that the central groove be somewhat longer than the surrounding grooves. The lengths of all the grooves may be extended in piecewise continuous fashion to create repeating zones of proximity along the axial extent, thereby forming 'distributed' sensors that have proximity that repeats at multiples of the wavelength of the helix of the rope windings within chosen axial limits.

At each zone of close proximity, the grooves on the two fibers may be proximate for one turn or several, within a limit of 180 circumferential degrees. The sensors are arranged in triads so that sensors in each triad are at significantly different circumferential orientations, preferably near 120 degrees apart. It should be apparent that the function of the grooves, which can be circularly symmetrical, is analogous to the function of the circularly symmetrical loss region shown in FIG. 18, i.e. a circularly symmetrical entity is transformed into a sensor with a circumferential orientation, due to the cyclically repeating structure of a helix.

Figure 28B:
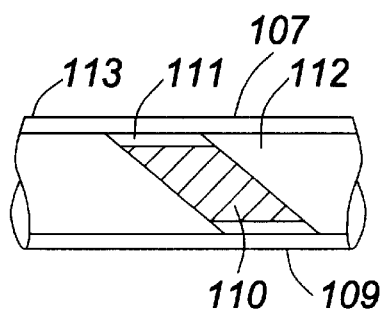

The capacitance sensing structures are explained in more detail by reference to FIGS. 28*b*, 28*c*, and 28*d*. FIG. 28*b* shows a partial turn of a groove 109 in a typical fiber 107. The groove exposes a central conductive wire 110 covered with an insulating layer 111, shown transparent in FIG. 28*b* for illustrative purposes. The insulating layer is surmounted by a conductive layer 112. The 'groove' is formed by a discontinuity in the conducting layer. Another layer 113 can be used on the central fiber 107, to enable twist sensing. The twist sensing layer is a compressible insulator that may be a homogeneous film, or a spiral wrap of compressible insulating fiber. It keeps the surrounding fibers at a slight radial displacement that gets modulated by twist. The same methods used to enhance twist sensing in the optical fiber examples may be used to impart a pre-wind to the twist sensing zone or to make it insensitive to bending. Twist will create a 'common-mode' response in all three sensors of a triad, whereas bend will affect at least one of the fibers less than the others.

Figure 28C:
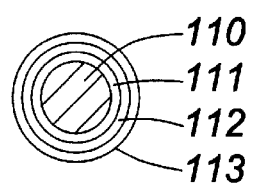

FIG. 28*c* shows the various layers in a cross section not including the groove. A very thin coaxial wire may be made by coating a bare metal wire 110 with a thin insulation coat 111, then depositing metal 111 on the insulation coat. The groove may be formed by etching off the metal, or masking its deposition in a groove shape. The deformable twist sensing layer may be deposited or wound over all. If wound, the winding would normally be clockwise if the groove is counterclockwise.

Figure 28D:
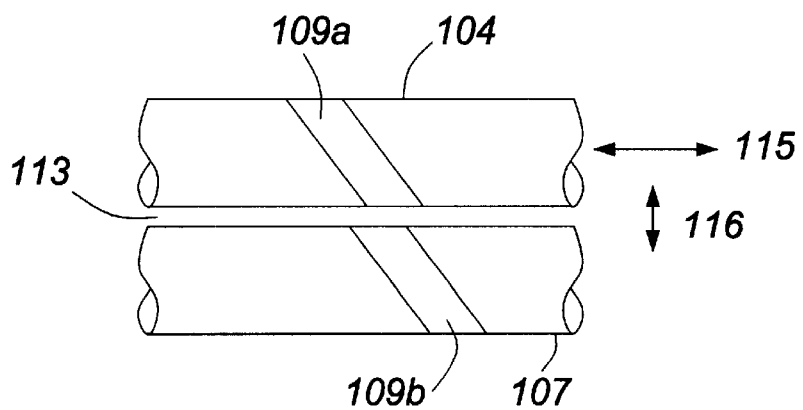

FIG. 28*d* shows a typical surrounding fiber 104 separated from the central fiber 107 by a thin twist-sensing layer 113.

During bending of the rope, fiber 104 will slide relative to fiber 107 in an axial direction shown by the arrow 115. The sliding is maximum if fiber 104 is on a portion of its helix bent outward with an orientation most closely matching the plane of the imposed bend. The sliding causes the electrical field coupling between the two grooves to change. If the grooves are arranged axially to be semi-overlapped when the rope is straight, the coupling will change in bipolar fashion. Width and pitch of the groove may be designed to maximize the coupling and its modulation. Coupling is significant only where the grooves face each other in close proximity; other parts of each fiber are shielded from coupling by the conductive layer 112. During twisting, all three surrounding fibers in a triad wind up or wind down, compressing or de-compressing the resilient layer 113 as indicated by arrow 116. This causes an overall modulation of all three couplings. Calibration is analogous to the methods cited for optical sensors.

Coupling modulation may be measured by well-known capacitive sensing art, such as by introducing an AC or pulsed signal on each of the surrounding fibers in turn, and measuring the current coupled into the conductive core 110 fiber 107 when it is connected to a resistive load. Normally, the shield layer 112 is at neutral potential with respect to the signals, or, in accord with known art, on receiving fibers it may be 'driven' with a sample of the received signal to minimize attenuation and also prevent pickup from other sources. It is also possible to build a capacitive sensing rope that measures coupling between adjacent surrounding fibers, since the slippage varies as a cosine of the circumferential orientation. In that case, the central fiber can be inactive or absent, and the surrounding fibers can be 'read out' in adjacent pairs by injecting a signal into one pair mate and reading the current in the other pair mate. Typical injected signal voltages are in the 3–20 volt peak—peak range.

A rope 99 comprising strands 100' of seven optical fibers each is shown in FIG. 30. In a construction reminiscent of the strands of fibers (such as FIG. 21), the rope of 7 strands contains a central strand surrounded symmetrically by six strands. Usually the central strand will be sensitized, whereas usually a central fiber in each strand will not. Usually the rope will be formed by winding strands in a counterclockwise direction if the strands themselves are wound clockwise, or vice versa. This counter-rotatory principle is illustrated in FIG. 30, showing the rope, and FIG. 31, showing one of its strands.

FIG. 31 is a detail of strand 100' of rope 99 in FIG. 30, and is representative of strands in general. Fibers 101, 102 and 103 are treated with one triad of sensors, with bend-loss-sensitized zones 110, 111, and 112 respectively. Another triad is formed by fibers 104, 105, and 106 and zones 113, 114, and 115. Zone 115 is hidden by the other fibers. In this example, the sensitized zones are more than one pitch long. Zones 113 and 114 are long enough to show up twice along the strand, and are marked 113A, 113B; and 114A, 114B. Zones 110, 111, and 112 are shown for only a short portion of their length. The loss zones are depicted as hatched rectangles, with exaggerated size where shown at the cut ends of the fibers at the left end in the figure.

FIGS. 32, 33, and 34 show sections through the strand of FIG. 31, at stations 117, 119, and 118, which are at approximately two ends and the middle, respectively, of a pitch length (complete turn of a helix). The three sections reveal that the fibers surrounding the central core 107 remain in the same circumferential order, but rotate by approximately 180 degrees at each station. Nevertheless, for reasons explained earlier, the zones continue to face at the same angles in any section, if the strand is built without adding twist to the fibers. The zones are shown diagrammatically as chord lines.

Figure 34A:
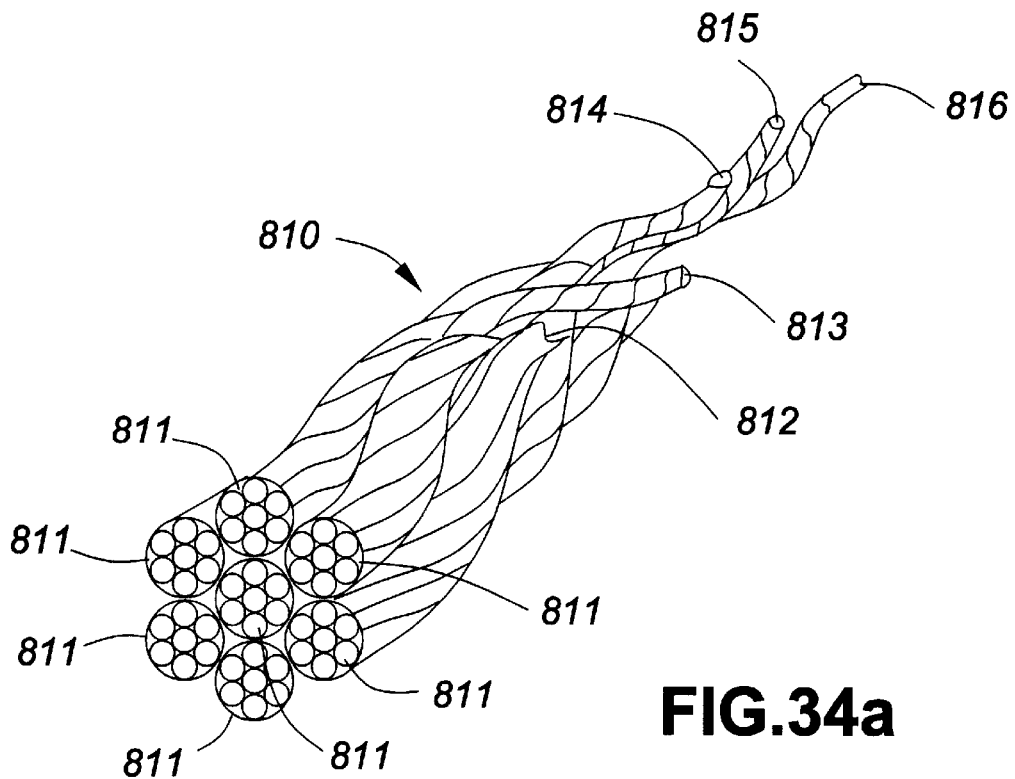
FIG. 34a shows a stranded rope which is tapered.

FIG. 34a shows a variation of the stranded rope of FIG. 30, in which the strands are not all the same length, resulting in a tapered rope. Each strand is only as long as required to reach a desired axial sensing location. This ensures that more distal portions of the rope are as small and flexible as possible, which is often important in medical applications. The rope 810 is comprised of strands 811, which end in reflector structures or nested return loops at locations 812, 813, 814, 815, 816, and a sixth location not shown because it is behind the rope. In analogous fashion, a strand such as that illustrated in FIG. 21 could be comprised of fibers each ending in a mirror at different axial locations. The strands of fibers may be held in place at least near their distal terminations by adhesives, helical wraps of fine fiber, or by compressive bands.

Figure 34B:
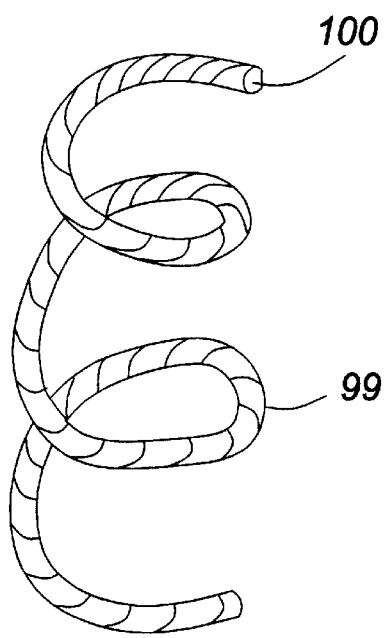
FIG. 34b shows a rope as in FIG. 30 formed into a helical shape to provide an extensible cyclical sensor.

An elongate sensor structure such as a ribbon or rope may be further formed to have additional overall sinuations. A rope form of such a 'doubly formed' sensor is shown in FIG. 34b. The rope 99 is comprised of strands 100, made of formed fibers such as fibers 101 through 107 of FIG. 32. The rope has been formed into a helix, for example by winding it on a cylinder and heating the rope to near the softening point. When cooled, the rope will maintain the overall helical shape. Since it is already fitted with sensor fibers that report the position and orientation of all portions of the rope, extension of the resulting structure can be sensed, along with its overall shape. The result is an extensable cyclical sensor. It could be used, for instance, surrounding an arm or leg, in which case joint bending and limb rotations could be sensed for various limb lengths. It could also be used to measure displacement in 6 degrees of freedom between two moveable objects.

A doubly formed sensor may also be retrofitted to a flexible member to provide measurement of the member's six degree of freedom position and orientation. Examples include fitting it around a flexible endoscope, or fitting it around a computer mouse cable.

Figure 34C:
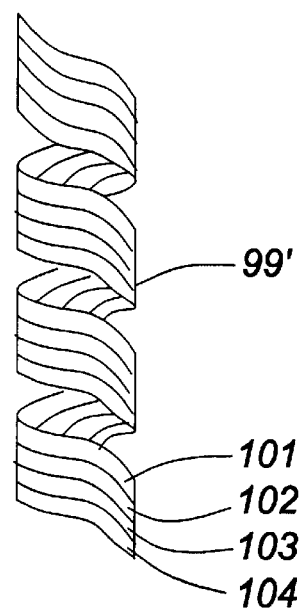
FIG. 34c shows a ribbon of parallel, mutually supporting fibers formed into a helical shape to provide an extensible cyclical sensor.
Figure 46:
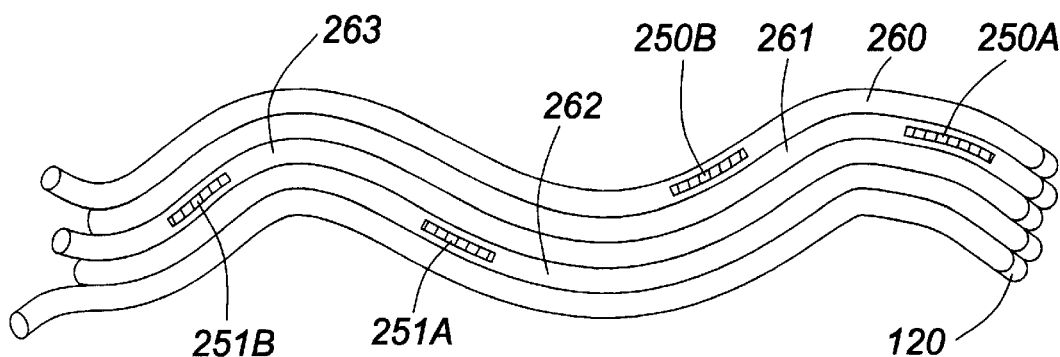
FIG. 46 shows details of the sinuated structure of FIG. 45.

An analogous ribbon-form extensable sensor is shown in FIG. 34c. It is comprised of ribbon 99' which is in turn comprised of fibers 101, 102, 103, and 104 (the number is limited for ease of illustration) that are capable of sensing bending relative to the ribbon, but when doubly formed, are capable also of responding to twist of the doubly formed member. The ribbon shown in FIG. 34c could also be replaced by a wavy ribbon as illustrated in FIG. 46, in which case it would sense twist and bend even when not doubly formed.

The sensor illustrated in FIGS. 34b is a cyclically repeating sensory structure with three principal spatial frequency components which may be described by the three dimensional waves formed by the space curve of each component part. One is the helical wave of each fiber within a strand. Another is the helical wave of each strand within the rope. The third is the helical wave of the overall sensor. The third wave form tends to impart greater accuracy to some measurements, because such a structure can conform to shapes with little likelihood of having abrupt localized bends or twists.

Another form is shown in FIG. 35, which depicts a cylinder 411 made of ribbons of three fibers such as 412, 413, 414. The ribbons 415 are interwoven. Bend and twist sensitivity is added through treatment, shown for example at 416A and 416B, which together depict a bend and twist sensing pair. In this case the twist sensing is not always needed, because the structure, if placed on a central core such as a flexible endoscope or hose, allows almost no twist. The cross section through the cylinder at 417–418 is shown in FIG. 36. The interwoven structure of FIGS. 35 and 36 is commonly used to surround bundles of electrical cable. Its diameter can be expanded by compressing axially, or shrunk by stretching.

FIG. 37 shows the cylinder of FIG. 35, with the end 425 in round shape, indicating the overall cross-sectional shape. FIG. 38 is an oval form of the same weave, which may be used on oval inclusions, in which case it will be somewhat sensitive to bending. 40 shows a cross section through a double-walled form of FIG. 35. Each wall is bu The form of FIG. 39 is almost flat, like a ribbon, in which case twist sensing is very appropriate. All three forms may use the same sensors as shown in FIG. 35. Figure ilt like that of FIG. 35. The double wall tends to prevent collapse laterally, and is resistant to twisting.

FIG. 41 shows a woven structure such as that of FIG. 35 capable of covering a structure such as a balloon 453. The balloon can be inflated through tube 452 and its shape sensed by bend sensors included in the weave. This is applicable to angioplasty or to sensing expansion of tubing and pipes. The woven structure is also self-supporting. It may be formed by axially compressing the weave without an included balloon or pipe. The sensors may then be used to measure the axial displacement of the compression, as well as any bend or twist produced by the forces and moments applied at the ends. It may also be placed over a finger or other limb to sense bending in two degrees of freedom. FIG. 42 shows a spherical end weave enclosing a ball.

In all constructions involving wrapping of a core, the core may be removed after wrapping. The space may be used for other functions. In all constructions, the fibers may be impregnated with polymer, such as polyurethane, flexible epoxy or silicone, to provide protection or tailored resilience. Ropes and cylinders of fiber may of course be placed inside tubes for similar purposes.

Figure 43:
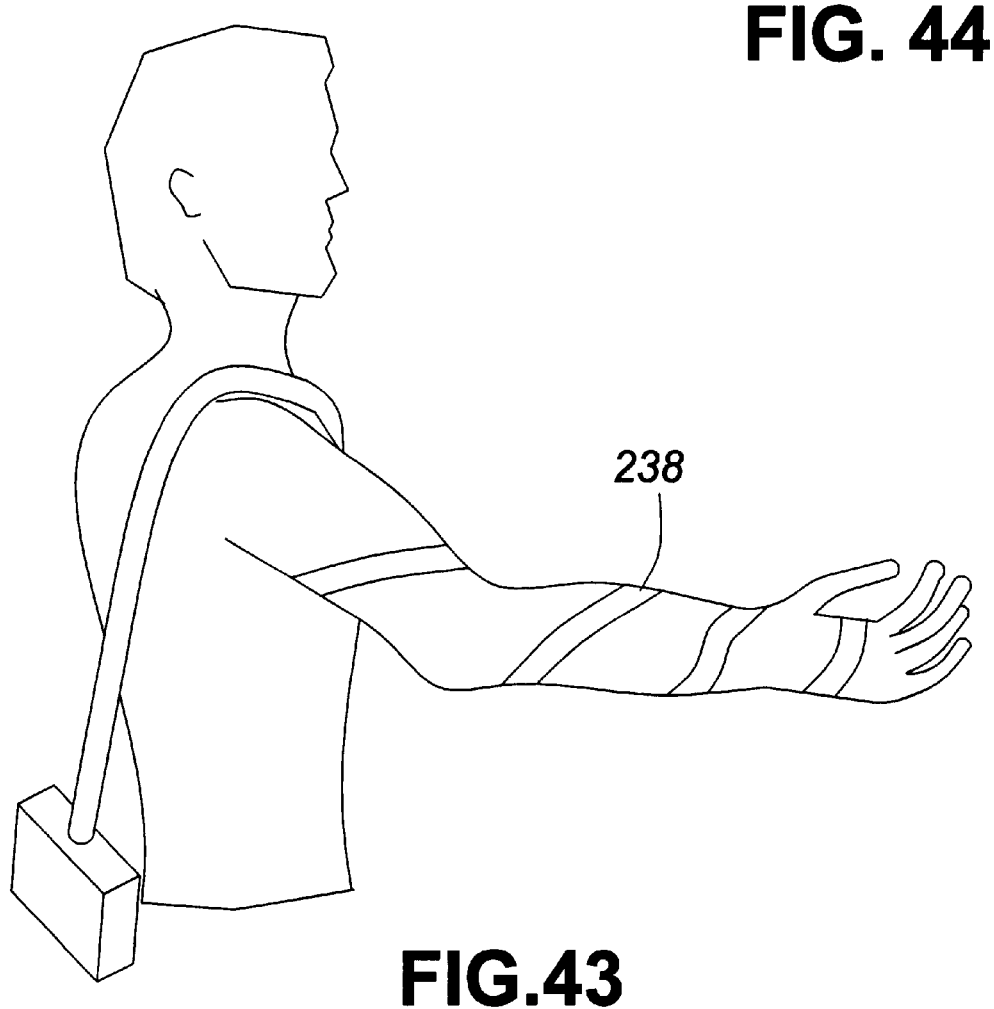
FIG. 43 is a pictorial depiction of a person wearing a ribbon-type sensor to capture motion on a video display.

FIG. 43 shows a helically-wrapped tape (ribbon) or rope form of the sensor array called a 'strip' for simplicity. It is wrapped about a human back, arm, over the upper arm, forearm, and hand. The generally helical wrap allows the strip to conform closely to the contours of the human form, with its broad surface (if it is a tape) running along the skin. Even the portion on the back is roughly helical, because it purposely begins on the left waist and passes over the right shoulder in a path including bend and twist. This is important in allowing it to follow the bending of the back without requiring mechanical contrivances such as a slippery channel of cloth, to accommodate slippage between back and tape. The strip may include sensors placed continuously from the interface box to the tip of the strip. Similar installation is possible on legs and on neck and head to capture full-body shape and motion. The helical configuration imparts useful properties including close fit, integrity of form, extensibility without requiring slippage, and highlighting of key features for use in mathematical construction of skin and bone models. The advantages apply to sensors of the prior art patent '672, as well as to the rope and textile forms described in the present disclosure, and will now be explained.

Close fit of a helical form is enabled because a bent and twisted sensory member may lie flat against a curved surface even if the member has a wide rectangular cross may be used. The signal wires may also be inside the core, and only strain wires would be on the outside. The sensitive portions can be arranged in arrays similar to those used with optical fiber arrays, with sensitivity at specific axial section.

A helical form is nearly self-maintaining, so can be said to have integrity of form. If removed from the limb without being unwound, it will tend to maintain helical shape. If incorporated in a sleeve or trouser, the garment comprising cloth and sensor strip will take on a cylindrical shape due to synergy between the helix forces and moments and the tension imparted to the garment. Even without an added garment, the helical form is maintained even when the sensor is in only partial contact with the limb, thereby aiding in a smooth measurement of the overall form of the limb.

A helical form has extensibility without requiring net end-to-end slippage. This is important in following motions of the back or limb. The sensor can extend or compress with the motions by virtue of bends and twists distributed smoothly along its length, extensions being balanced by compressions on successive half turns, without requiring added mechanical contrivances to accommodate additive length differences inherent in axially placed sensors.

Automatic 'feature finding' is a valuable property imparted by cyclical structures fitted to arms and legs or other appendages. For example, the sensor strip of FIG. 43 can be fitted to limbs of various lengths while always being arranged with the same number of turns per limb segment. In FIG. 43 the strip has 1.5 turns around the upper arm and lower arm respectively. If the arm is held in a standard pose (a 'homing' pose), such as straight in front, horizontal, with palm down, the repeating cycles of bend of the sensor may be used in automatic software algorithms to define key features along the arm for use in forming a mathematical and graphical model of the arm including skin and bones.

A preferred means of automatically finding features is to calculate an 'end—end' line in three dimensional space from the beginning of the sensor region at the interface box at the waist in FIG. 43, to the hand. Distances from the end—end line to all portions of the sensor strip may then be calculated, by erecting, mathematically, lines orthogonal to the end—end line and touching each portion of the sensor strip. If these distances are plotted against increments along the end—end line, a sinuous curve results. The first peak along the curve is the shoulder. If there is one turn of the strip from shoulder to elbow, the next peak locates the elbow. If there is another turn around the forearm, the next peak locates the wrist.

Other key features may be located by finding the minimum distances, or valleys, which will be approximately 180 degrees around the helix compared to nearby peaks. Interpolation can be used to find 90 degree or finer features as well. If these features are stored during capture of the homing pose, they can be used subsequently for all poses to identify locations along the sensor strip that correspond to the key features. The key features permit calculation of models for skin and bones.

The method provides skin and bone models that will be scaled to the individual wearing the sensor strip, regardless of limb size. This is done without any separate measurement of limb lengths other than performing the 'homing' pose with the strip wound with a known number of turns per limb segment. Naturally, the homing pose can also be used to set a scale for the length of the limb and the location of all the features, again using no measurement instrument other than the sensor strip during the homing pose.

Two homing poses such as the above horizontal one and another with a slight vertical lift such as holding the hand 20 cm higher vertically, can also provide a means of orienting the data set for the limb in a known relationship to the axes of a virtual environment, and for orienting multiple limb data sets (such as for arms and legs) to all have the same relationship to a virtual environment or World Coordinate System.

Bone models can be calculated by using the 'R' vectors that span from the start of the sensors (the interface box in this case) to each point along the sensor strip. First, a virtual curve is calculated using a moving average of the R endpoint values along the sensor strip (by average we mean a vector having x, y, and z components wherein the x component is the sum of the x components divided by the population, and similarly for y and z). For instance, if the average includes approximately half of a turn of the helix, the curve will lie near the center of the helix. The curve will have some waviness of helical form, but of reduced amplitude. The population (number of vectors averaged at a time) can be used to reduce the waviness. Portions of this central line can be used to define bones. The portions are determined by using the key features, so that for instance a lower arm 'bone' can be calculated as a straight line between the averaged R vectors near the elbow and the averaged R vectors near the wrist.

A 'skin' model may be formed by connecting cyclically repeating points along the tape with lines that lie approximately axial to the bones. The combination of a 3D curve representing the sensor strip and the 'axial' lines forms a visually compelling surface indicative of the skin. As an example of repeating points, the axial center of each sensor may be connected analytically to the axial center of the next sensor. The connecting lines will typically have a helical form with pitch dependent on the points chosen. Spline functions may be applied to refine the model to a surface.

Other lines forming chords of the helical curves may be used to determine heading vectors for the 'bones', so that the bones have not only 3D coordinates for their ends, but are associated with orientation information, such as roll, pitch, and yaw angles. For instance, a chord connecting two feature points on a tape under the forearm can be reduced to a unit vector and used to find a cross product between it and a unit vector form of the forearm line. The resulting cross product vector will point approximately vertical during the homing pose, and will follow the roll of the forearm for all subsequent poses. The homing pose may be used to 'zero' the roll angles so that they are defined as deviations from the roll of the homing pose, so that 'approximately vertical' during homing can be upgraded to 'exactly vertical'.

Once 'skin' and 'bones' are known, one also knows the radius of the limb at all points along its length, and can use variations in radius to determine muscle contours.

The above method uses all parts of the sensor strip to define the bones and skin features. It is more robust to movement and changing skin contours than one based on sensing of an individual, isolated point near each joint.

Figure 44:
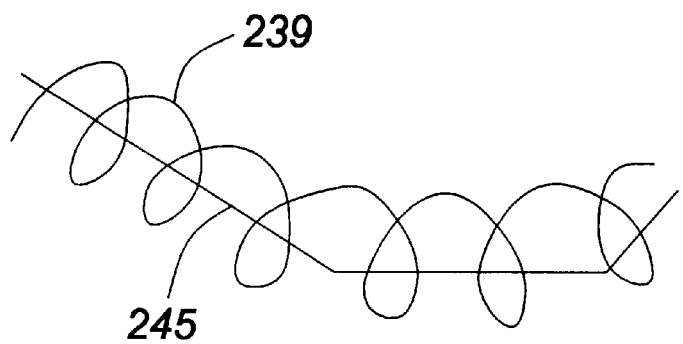
FIG. 44 is a diagram of the helical structure of FIG. 43.
Figure 45:
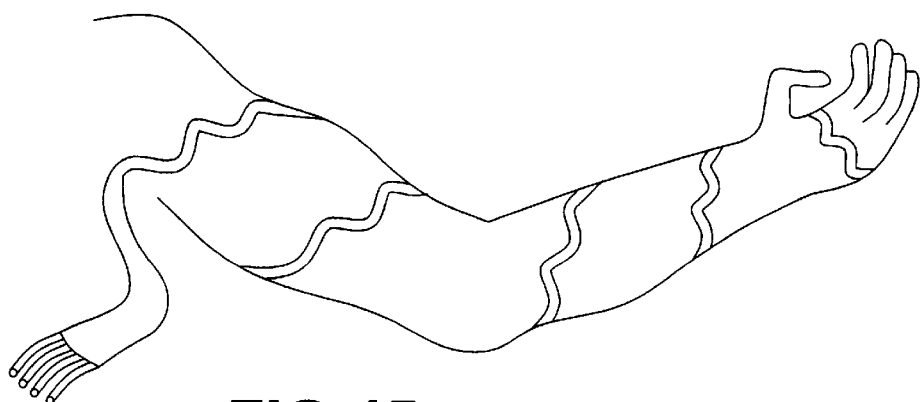
FIG. 45 shows a similar ribbon but sinuated.

In a variation shown in FIG. 45, the tape on the arm is wavy or sinuated within its plane. The detailed construction is shown in FIG. 46. A 'ribbon cable' of side-by-side fibers is sinuated within its plane. Mirrors 120 are used to return light to couplers at the other ends. The construction may also employ loops to return light. In the small piece of this sensory tape shown, each fiber is treated at one location. In practice, it is often desirable to treat the fibers at multiple locations, to distribute the sensing of bend and twist over a larger extent. Each pair of fibers, such as 260–261 or 262–263, forms a bend-twist pair, because treatments 250A and 250B are approximately orthogonal along major twist axes, as are 251A and B, and these sensor portions are oblique to the median as shown at 245 in FIG. 44. The sinuation permits the sensing of both bend and twist, and reduces any stretching effects due to bending. The fibers may be held at the neutral axis of a flexible encasement, or the fibers may be glued together side-by-side and used with little or no other support.

As indicated, a ribbon of this kind can be made by gluing together sinusoidal fibers. If such fibers have their neutral axis strictly sinusoidal, the edges of the fibers which connect to other fibers are not truly sinusoidal, meaning that they only connect at certain points. Such a structure can however also be made of wavy fibers which are glued along their lengths; however in this case only one of the fibers will be truly sinusoidal.

In this example we have shown treatments on one side of the ribbon. This is a convenient form for manufacture. In some applications where bend or twist are concentrated spatially, the difference in axial location of the pair members 250A and 250B or 251A–B, may be undesirable. In that case, it is possible to treat pair members such as fibers 260 and 261 on opposite sides of the ribbon, respectively, in the same axial location. In that case, the treatments will face in opposite directions so that bend and twist may be resolved uniquely (the sensors will produce opposed signals for bend and common mode signals for twist).

Figure 45A:
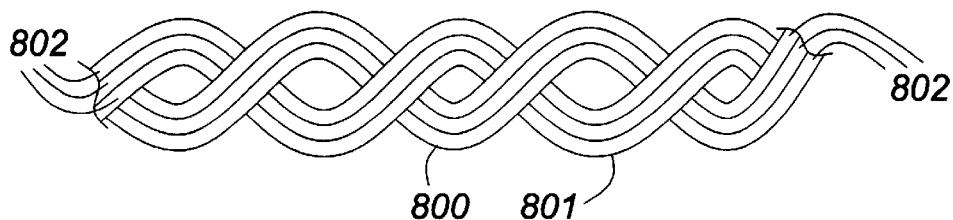
FIGS. 45a and 45b show composite members each having two sinuated ribbons.
Figure 45B:
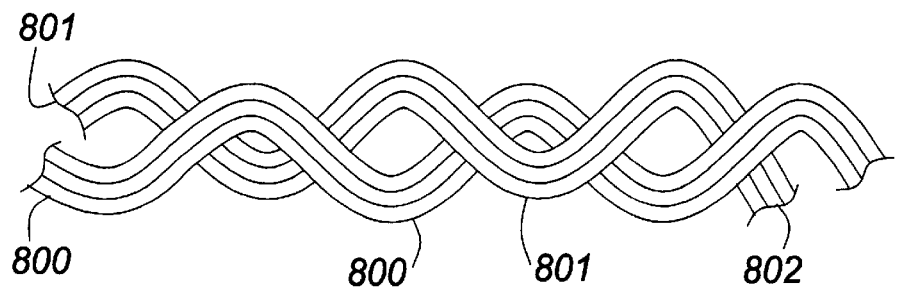

A ribbon wavy within its plane can become a constituent 'strand' of a 'flat rope.' This is accomplished by interleaving alternate waves of one ribbon with those of another. If the waves of each ribbon are in the 'XY' plane of the ribbon, then the interleaving creates a waviness in each in the 'Z' dimensions out of the plane of the ribbons. The combination of the two ribbons is now a 'member' that can be freely bent and twisted. As with a helically wound rope, the surfaces of waves with normals that face out from the bend will curve more than the surfaces of waves with normals facing in toward the center of bend. The net extension and compression will be zero, as in a more 'three dimensional' rope. The construction may be exploited to double the number of sensors with minimal increase in size or stiffness of the member. Each ribbon may have sensors that all face outward from the neutral axis of the member, or each may have a mix of facing directions. A third ribbon may also be interleaved, and the interleaving may be extended to any number of ribbons to create a surface of arbitrary extent. Even though the fibers are no longer in the neutral axis of the member, the 'flat rope' bends and twists without requiring net slippage between the ribbons along their total lengths. Two interleaved ribbons 800 and 801 are shown in FIG. 45*a*. The ribbons are planar, wavy within their planes, and comprised of fibers 802. A variant interleaving method is shown in FIG. 45*b*).

We have now shown that sensor treatments revealed in the '672 patent and its prior art may be used to create sensors on fibers and the fibers may be interrelated mechanically to form a sensing member without requirement for a separate mechanical substrate. The member takes on mechanical and sensing properties not present in the individual fibers. As indicated above, other optical fibers may be added for use as reference fibers, as illumination fibers, or as return light fibers.

Working prototypes of ropes have been made using 0.25 mm plastic optical fibers. They consisted of six strands of looped fibers, each strand being 0.75 mm diameter, holding one triad of sensory zones. The 6 triads allow the rope to sense 3D shapes. Other ropes have been made with mirrored ends and with directional couplers, and with most of the variations presented in this description, including two- and three-fiber ropes, distributed sensors along ropes, counter-rotated layers upon larger substrate fibers, twist enhanced zones for sensing twist, and added helical wire for producing twist and bend sensitivity without other treatment of the fibers. Flexibility and strength of the prototypes are similar to those of nylon mechanical ropes. Positional resolution at the end of a short (15 cm) rope was better than 1 mm. The efficacy of the helical wrap of a tape around human limbs and mechanical links has also been proven through prototyping, yielding accuracy and compactness exceeding that of antecedent configurations of the ribbon form of the art. Also, various other packings have been demonstrated, such as multiple-layer ropes and woven ropes. The same packing rules that direct rope and cable manufacturers direct the construction of sensory ropes. Convenient, compact and flexible ropes can be formed of two, three, seven, 13, 20, etc. fibers packed around a central core or forming their own support. Generally it is advantageous to use strands of fibers rather than pack too many fibers in one uniform rope.

The presence of strands enables various axial and lateral array organizations within a rope or braid, and there are analogies to the 2D organization of textiles as well, as discussed below. For simplicity of wording we will use the example of a 'rope.' For example, each strand may contain axial loci where all the bend and twist sensing for that axial locus on the rope is desired. We use the term locus because it may refer to a point (or near-point, since all sensors have some extent), or a significant length, as when distributed sensors are used. Alternatively, a strand can contain fibers having one kind of sensor for all loci along the rope, such as all the 'X' bend sensors. Another would contain fibers having all the 'Y' bend sensors. Another would contain all the 'twist' sensors. More generally, by 'X', 'Y', and 'twist' we would mean 'sensors generally oriented at approximately x degrees circumferentially', 'sensors generally oriented at approximately x+120 degrees circumferentially,' and 'sensors generally oriented at approximately x+240 degrees circumferentially.' We might also replace the terms 'all the 'X', etc.' with 'a certain number of the 'X' etc.' sensors, in order to reduce the size of strands or to accommodate more sensors within a rope. In another variation, we would use redundant sensors within a rope or strand. The redundancy can be used to improve accuracy, by solving more than three equations in three unknowns at each locus, or to select sensors with the best orientations and not bother to use the rest, or to provide for breakage. Redundancy may be particularly important for textiles and clothing, where some breakage and difficulty in calibration are expected.

It should also be clear that the invention need not be comprised of optical fibers, but may be comprised of other fibers such as electrically resistive fibers, for example strain gauge wires sensitive to bending or strain upon bending, or similar constructions of conductive polymeric fiber. This principle applies to ropes, strands, and cloth forms. The constructions also lend themselves to capacitance sensing, whereby modulation is achieved by bend and twist bringing fibers into greater or lesser proximity within a region. In all the electrical constructions, insulation may be used to isolate the conductors on adjacent strands or to produce known dielectric properties for capacitance sensing.

Figure 47:
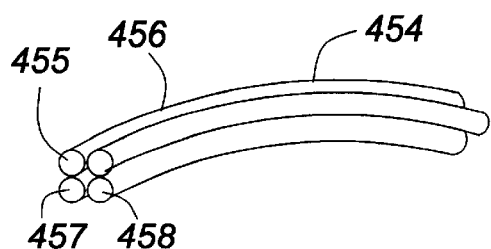
FIG. 47 shows a perspective view of a simple sensing member formed of wire.
Figure 48:
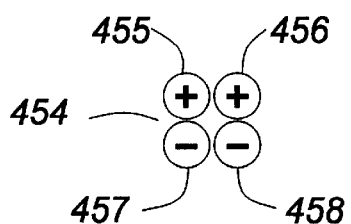
FIG. 48 shows a cross-section through the member of FIG. 47.

A bipolar strain gauge sensor structure 454 is shown in FIG. 47. Wires 455, 456, 457, and 458 are sensitive to elongation because their resistance changes with strain. The four together may be used for bipolar bend-sensing in two axes. This is shown in FIG. 48, a cross section through the downward-bent structure of FIG. 47. The bend places upper wires 455 and 456 in tension and lower fibers 457 and 458 in compression. Bridge circuitry may be used to measure the bend in both the vertical and horizontal planes. A commercial device for two-axis bend sensing (manufactured by Biometrics Inc.) is based on similar principles.

Figure 49:
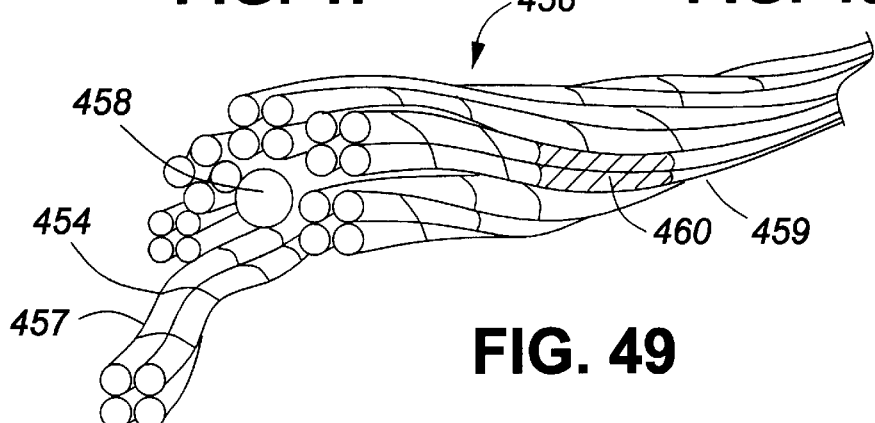
FIG. 49 shows a rope made from sensing wires in accordance with the invention.
Figure 50:
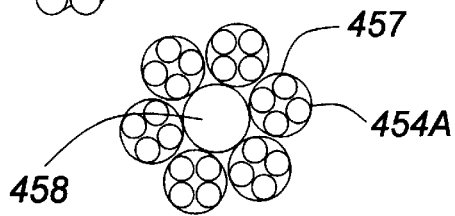
FIGS. 50 and 51 are cross-sections through the rope of FIG. 49.
Figure 51:
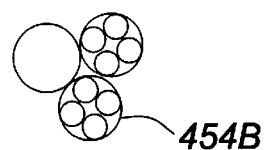

A rope in accordance with the present invention, based on the sensor of FIG. 47 is shown in FIG. 49. The groupings 454 of wires are wrapped with small mechanical fibers 457 to allow the groupings to rotate about their axes and thus maintain a zero-twist condition when wound into the rope 456, around central core 458, which provides a space for return electrical connections. Sections, shown in FIGS. 50 and 51, taken at different axial locations, indicate the zero-twist condition by showing the group of four 454A and 454B at the same orientation even though at an arbitrary axial location.

The wires are comprised of signal-carrying portions 459 at the ends of strain-sensitive portions 460. The signal wires may be welded to the strain wires, or other connection means locations. The groups of four have the equivalent of a 'facing' direction in a specific plane. Each provides a reading of orthogonal bend components. Twist may also be sensed by adding more strain-sensitive wires, such as pre-twisted pairs in a fashion analogous to that described for pre-twisted optical fibers.

It should also be clear that subsets of the present invention, especially as it relates to optical fibers, are workable. For instance, a one-axis bend sensor may be formed by winding a rope, using a common 'bulk' illuminator for all the fibers, and sensing the return light simultaneously and additively from all the fibers with a 'bulk' detector (e.g. a photodiode and amplifier illuminated by all the return fibers). In this embodiment the sensor is formed by creating a loss zone along an axial line of the rope, wherein all the fibers in the rope are affected along that line. One may also alternate the fibers affected along a first line along the rope axis, then rotate the rope about its axis by 90 degrees or another desired angle, and treat the remaining untreated fibers. The two groups of orthogonally treated fibers may be sensed by two 'bulk' illuminators and sensors as in the single-axis case, and a two-axis bend sensor will result. Clearly, the principle may be applied to triads of sensors, and twist sensing may be added. Thus, the 'subset' may be turned back into the superset, with advantages. The advantages are increased light levels, and redundancy, should a fiber break.

It should also be clear that member in accordance with this invention as previously described may be a cloth rather than a rope. In this form, a sheet is comprised of the sensory fibers themselves, i.e. the fibers form the "substrate". Sheets of cloth made from sensory fibers may be flat or in the form of cylinders or balloon shapes, suggesting use as sleeves, volume sensors, airbags, angioplasty devices, breathing sensors, and the like.

Figure 52:
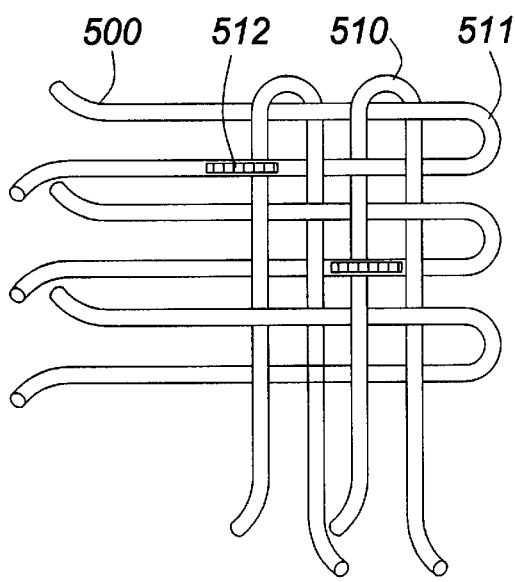
FIG. 52 is a view of a textile woven of sensing optical fibers in accordance with the invention.
Figure 53:
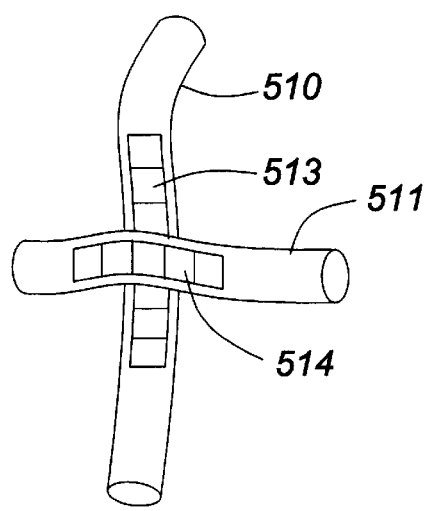
FIG. 53 is an enlarged view of fibers of the woven construction with sensing portions shown.

An example of a woven sensory sheet is shown in FIG. 52, comprised of optical fibers 500. Only one corner is shown, which includes warp 510 and weft 511 fibers which loop back at the upper and right edges respectively. In variants, the warp fibers would more likely be mirrored at the upper edge and would not loop back. At regularly spaced horizontal and vertical locations 512, sensor pairs are formed by treating the warp and weft fibers to lose light out of the plane of the woven sheet. Normally, a given fiber would be treated to lose light at only one or a few contiguous locations, so that two fibers are devoted to sensing curvature at a single crossing, or a small region near a crossing. Since weaving naturally produces diagonal patterns, both bend and twist sensing are provided by the pairs or groupings. A treated crossing is shown in FIG. 53. It comprises fibers 510 and 511 treated to lose light in narrow strips 513 and 514. The orthogonal arrangement is sensitive to all angles of bend and twist at that location, and all bend and twist may be uniquely determined at that location by calibrating the sheet with known bends and twists. The sensors can be addressed with light fed in and out at two edges, where the fibers can continue past the woven area and be grouped into bundles.

Figure 54:
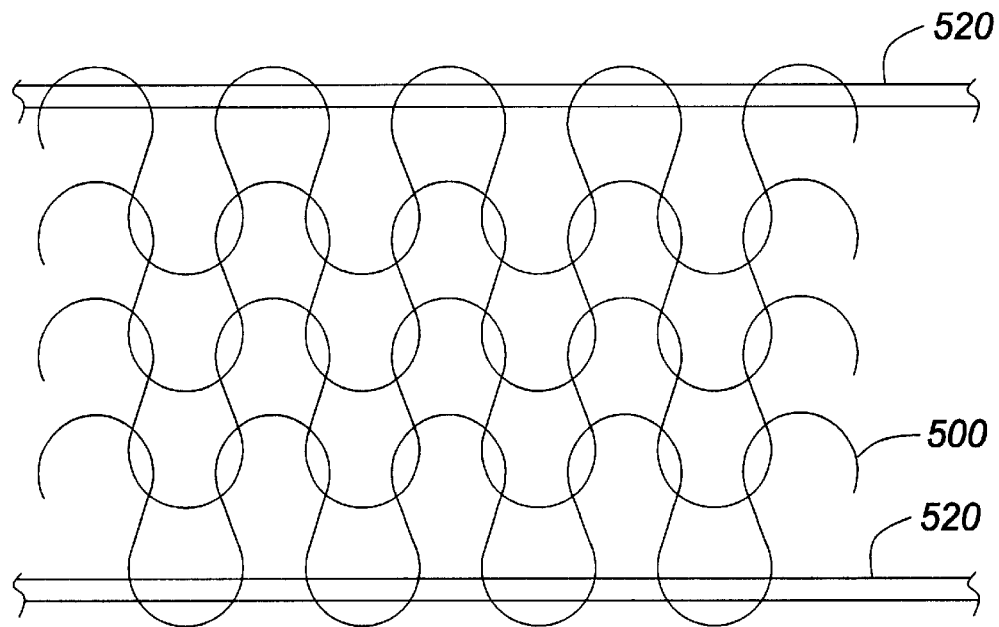
FIG. 54 is a view of a knitted construction using sensing fibers in accordance with the invention.
Figure 55:
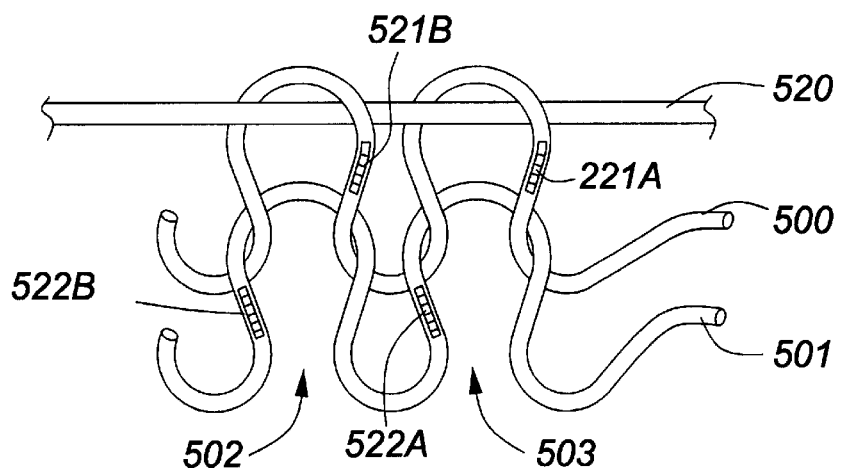
FIGS. 55 and 56 are views of components of the knitted construction.
Figure 56:
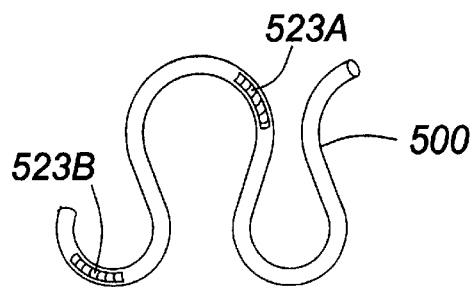

FIG. 54 portrays a narrow band of fabric knitted from optical fibers 500. It contains edge fibers or bands 520 that keep the edges from unravelling. The pattern is one of many standard knitted patterns, called 'plain.' Other patterns are described in (Von Bergen, Werner, 'Wool Handbook', Vol. 2, John Wiley, N.Y., 1969, pp. 583–632). Similar effects can be achieved with rib, purl, or many other patterns. Although drawn as a planar form, the knitting can encompass a volume, in the same fashion that socks and sleeves encompass a cylindrical or other volumes. Each fiber forms a 'course'; each vertical column of interlocked loops forms a 'wale'. The fabric of FIG. 54 may be sensitized by treating the fibers at selected locations. This is shown in FIG. 55, where fiber 500 is treated at locations 521A and 521B, and fiber 501 is treated at 522A and 522B. Treatments 521A and B have an approximate 45 degree orientation to the right of vertical ('+45 degrees'), whereas treatments 522A and B are oriented by approximately the same angle to the left of vertical ('−45 degrees'). Thus, fibers 500 and 501 form a sensor pair capable of sensing bend and twist along courses defined by fibers 500 and 501, distributed over two of the wales, 502 and 503. The same effect is produced if each fiber is treated as in FIG. 56, where two treatments 503A and 503B are formed for each sinuation, both at +45 degrees, or both at −45 degrees. In this example, all the fibers could exit the sheet or volumetric sensor at one edge, or two opposite edges, since all fibers run in 'horizontal' courses, not along wales.

Figure 57:
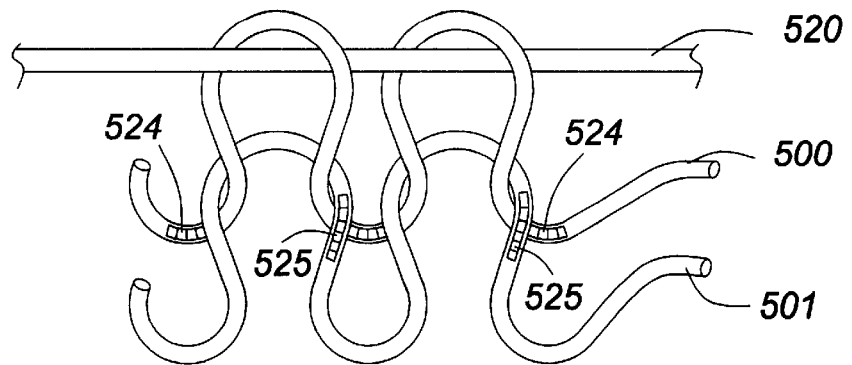
FIG. 57 is a view of another knitted construction.

FIG. 57 shows another treatment configuration, with horizontal treatments 524 on fiber 500 and vertical treatments 525 on fiber 501.

Figure 58:
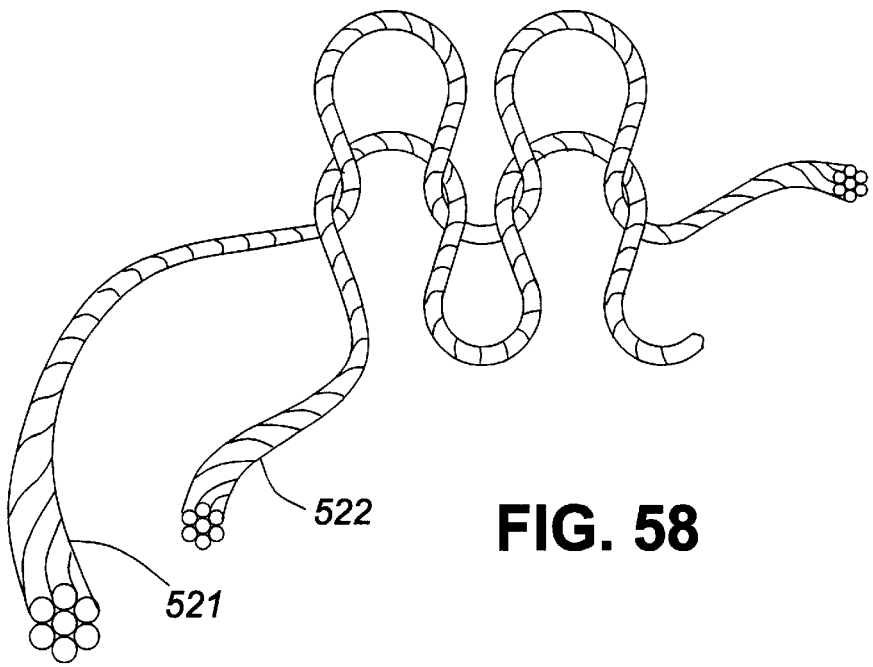
FIG. 58 shows two sensory ropes knitted together.

FIG. 58 shows two sensory ropes knitted together, as an example of a portion of a sensory fabric. This method allows many more sensors to be incorporated in a fabric, and is more independent of stretching effects that would change the angles of the sensors in the fabrics knitted from single fibers, in ways that would not be properly sensed. Pressure sensitivity can be reduced by incorporating cut-off 'plush' or velour strands, that will stick out and prevent pressure from compressing fibers upon other fibers. Otherwise, pressure sensitivity at crossings can be exploited to produce combined shape and pressure sensing.

Since the sensory ropes of FIG. 58 can be considered to be 'doubly formed' into sinuations, they have the same properties as the doubly formed helixes shown in FIGS. 34b and 34c, namely the ability to measure in 3D and six degrees of freedom, combined with extensibility. In this case the wave form of the sinuations is not helical, but rather a nearly two-dimensional wave that can be maintained either through multiple contacts with other ropes in the textile or by heat-forming, or by a combination of heat-forming and contact. Adhesives may be used instead of heat-forming.

Figure 59:
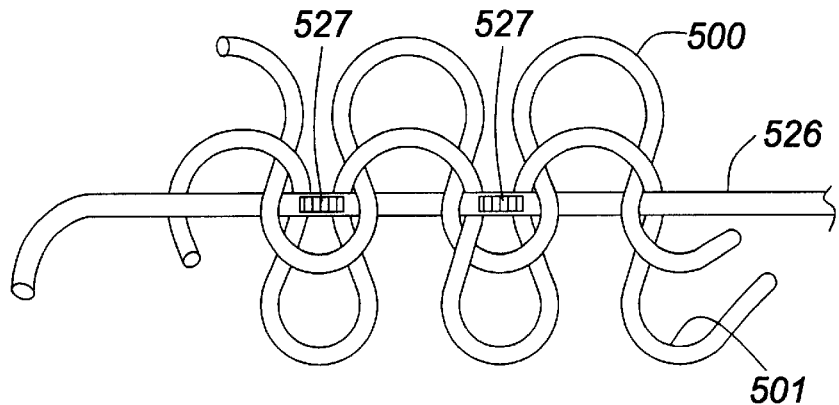
FIGS. 59 and 60 show further knitted constructions in which a straight fiber is also used.
Figure 60:
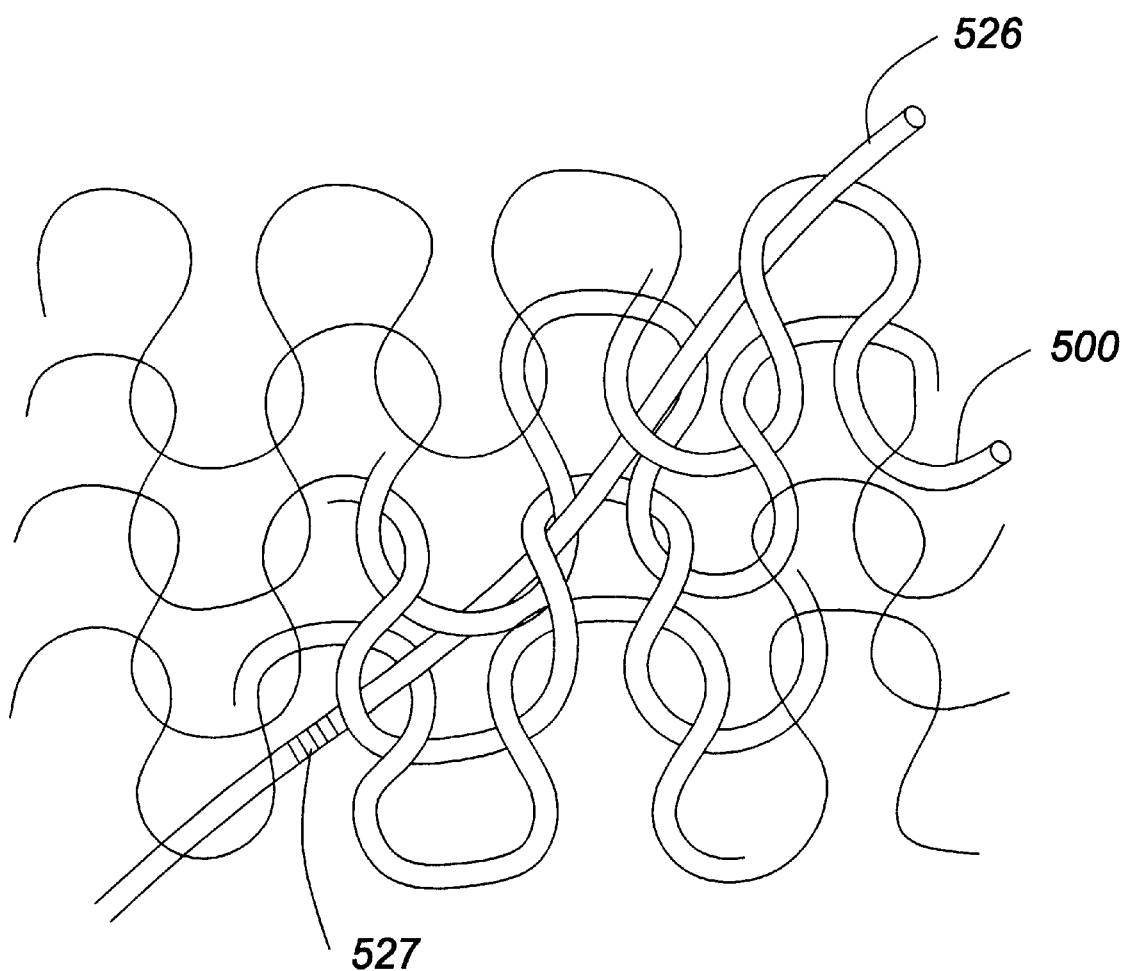

In FIG. 59 is shown a portion of a knitted fabric made with fibers 500 and 501, which includes a sensory fiber 526 with treatments 527, entrapped between the loops of two courses. This enables a combination of sensing on loops and on straight fibers. FIG. 60 shows fiber 526 entrapped diagonally in a knitted fabric. The horizontal and diagonal entrapments permit variations of bend and twist sensing within a fabric, and can increase the sensor density over that of looped fabric alone, without requiring a tight pattern that would induce too many microbending losses.

As seen above, with woven constructions, and with helical ropes and tapes as well, the claims/description of combined bend/twist and pressure sensing from this application and the '672 patent can be put to effect in ropes or cloth. Weaving and knitting form sinuated structures of fibers or strands that can be used to sense both shape (through overall distributed bend or twist response resulting from low-spatial-frequency bends) and pressure resulting from deformation of the higher-spatial-frequency sinuations.

As an extension of this principle, it is possible to form arrays that sense shape, pressure, and various other environmental variables, such as presence of liquids. The helical form lends itself to application of other sensory principles, such as those of recently filed PCT application No. PCT/CA00/00512. Thus, adjacent fibers along a helix can be coupled together by a lenticular layer of clear polymer to form a sensor that is responsive to bending and twisting of the helix. The lenticular layer may be coloured so that wavelength of the light used in sensing can be varied to access different sensor regions along the same two fibers (revealed in the above recently filed patent application for any two or more adjacent fibers simultaneously bent out of their plane). The lenticular regions also provide sensitivity to liquids or pressure, as described in the same recently filed application. End loops described in the same application may also be used to sense liquids or pressure.

In addition to lenticular forms, the helical and looped textile forms themselves may be adapted to sense pressure as well as shape. All that is required is a sensitivity to bending at a locale, and a means of transferring force to the locale, relative to other portions of the sensitive structure. For instance, pressure of a finger on a rope can affect the curvature locally, producing a modulation of throughput. Above, a fiber optic ribbon with sinuations was described wherein the sinuations can provide a means of sensing pressure. In helical form, sinuations are available in three dimensions, and may be similarly exploited. Calibration requires that there be sufficiently differentiated signals from bend and twist vs pressure. This may be satisfied by the same means employed in the sinuated ribbon; differentiation by relative spatial frequency content.

This description includes many sensor patterns that repeat over an extent, either with regularity, or with known irregularity. It has been shown that the 3D shape of the object may be determined from sensor outputs from the sensor patterns. The '672 patent includes a description of placing a ribbon sensor in a helical form and exploiting the known, constant fields of bend and twist along the helix to calibrate the ribbon as a sensor. The present application further exploits helixes and other repeating wave structures such as those found in knits and woven fabrics, to produce sensors that repeat their sensitivity at intervals with known orientation. The known orientations can be the orientation within the plane of a fabric, as in a crossed pair of treated fibers wherein the orientations are described by the angles of the fiber axes, or the orientation angle around the circumference of a fiber or a parent body such as a wound helix, wherein the orientation angle is the plane of sensitivity of the fiber sensor relative to an axis. Manipulation of the frequency of the repetitions can be exploited to produce spatially discrete or continuous sensors and arrays of sensors, to cover a broad range of desired spatial sensing attributes. In all cases, the exploitation involves manipulation of built-in bend and twist to enhance the sensing of applied bend and twist. Helixes are particularly suited to planned repetition, since they are completely described by bend and twist. Knitted and woven fabrics also provide a planned framework and method of construction for exploiting repeated sensing orientations, and also include known bend and twist in a less constant, but nevertheless repeating, way. All of these constructions may be produced without materials other than the fibers themselves.

Calibration has been described for a rope in reference to FIG. 16. Planar forms like wavy ribbons and interleaved wavy ribbons may be calibrated by means similar to that used to calibrate ribbons including substrates, as described in prior art patent '672. Planar textiles are calibrated using poses sufficient in number to include all the sensors in all their degrees of freedom. In all cases calibration requires solving simultaneous equations including a number of unknowns equal to the degrees of freedom within a given locus, and the number of sensors in said locus must be at least equal to the degrees of freedom, taking into account the known constraints that are present. Each equation describes the bend and twist presented to the sensors in the locus for a given calibration pose. If the sensors are nonlinear, poses must be included that are sufficient in number to characterize the sensor outputs at each desired level of intensity resolution. Accuracy figures were given in patent '672 for sensors including substrates. Accuracy of the present invention, for the case of a rope, is discussed just after the descriptions of FIGS. 44 and 45. Accuracy of all forms will tend to be improved over that of sensors with substrates because the formed fibers tend to have no net extension or compression, and thus no net slippage.

CONCLUSION

The foregoing has constituted a description of specific embodiments showing how the invention may be applied and put into use. These embodiments are only exemplary. The invention in its broadest, and more specific aspects, is further described and defined in the claims which now follow.

It will be appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

These claims, and the language used therein, are to be understood in terms of the variants of the invention which have been described. They are not to be restricted to such variants, but are to be read as covering the full scope of the invention as is implicit within the invention and the disclosure that has been provided herein.

We claim:

1. A measuring device for providing data corresponding to a geometric configuration in space, said device being in the form of a flexible, compliant, measurement member capable of bending in at least one degree of freedom, said member extending along a medial axis or plane and having spaced flexure sensors distributed at sensing locales having known locations on said member and separated by known sensor spacing intervals to provide flexure signals indicating the local state of flexure present at said locations;
   wherein:
   (1) the measurement member comprises a multiplicity of formed fibers,
   (2) such fibers being generally non-straight when the medial axis or plane of the member is respectively straight or flat,
   (3) said formed fibers including sensing fibers having sensing portions which provide said flexure sensors,
   (4) the sensing portions of different fibers being located at differing distances along said member so as to be located at said sensing locales spaced at said sensor spacing intervals,
   (5) the overall form of the measurement member being maintained substantially by the form of said formed fibers, alone or by their continuous or repeated contact with each other, to provide the strength or stability of the member.

2. A measuring device according to claim 1, wherein said formed fibers are mutually supporting by virtue of each fiber having continuous or repeated connections to others of said fibers along the length of the fiber.

3. A measuring device according to claim 1, wherein at least most of said formed fibers extend substantially the full length of the member.

4. A measuring device according to claim 1, wherein at least some of said sensing fibers extend substantially the full length of the member.

5. A measuring device according to claim 4, wherein substantially all said sensing fibers extend the full length of the member.

6. A measuring device according to claim 1, wherein only some of said formed fibers extend the full length of the member, said member being tapered.

7. A measuring device according to claim 1, wherein the stiffness of the member is not substantially greater than the total stiffness of said formed fibers.

8. A measuring device according to claim 1, wherein said formed fibers provide a major part of the tensile strength of the member.

9. A measuring device according to claim 1, wherein said member is substantially wholly constituted of said formed fibers, and wherein said fibers are optical fibers including said sensing fibers and other optical fibers used as reference fibers or illuminating fibers or light return fibers.

10. A measuring device according to claim 1 wherein said formed fibers are optical fibers and the sensing portions of the fibers are loss zones which are sensitive to their state of curvature by virtue of areas of their outer surfaces having been made absorbent to light passing along such fibers.

11. A measuring device according to claim 1, wherein said formed fibers are electrical conductors having axial zones the resistance of which is modulated by bending and twisting of said member.

12. A measuring device according to claim 1, wherein said formed fibers are electrical conductors electrically shielded from each other except in axial zones where capacitive coupling is enabled between chosen adjacent fibers, wherein the coupling is modulated by bending and twisting of said member.

13. A measuring device according to claim 10, wherein said formed optical fibers include fibers which maintain a non-straight form by reason of heat treatment.

14. A measuring device according to claim 1, wherein said member is formed as a cyclical structure made up of said formed fibers, which fibers provide said member with sensing locales distributed in a repeating pattern along said member.

15. A measuring device according to claim 1, wherein at least some of said sensing portions of the fibers are obliquely orientated to said medial axis or plane, whereby said member has sensing portions responsive to twisting of the member as well as sensing portions responsive to bending of the member.

16. A measuring device according to claim 1, wherein said measurement member is formed to have cyclically repeating sinuations, which sinuations provide extensibility which is measured by the sensing fibers as a consequence of their measurement of position and orientation along the length of the member.

17. A measuring device according to claim 14, wherein said fibers have cyclically repeating curves that take on cyclically repeating pairs of opposed deformations locally within each curve during curvature of the measuring device, without substantial changes in the net extension or compression of the fibers along the full extent of the device whereby said curvature can occur without overall slippage of fibers along their full length.

18. A measuring device according to claim 10 wherein said fibers have cyclically repeating curves and said loss zones placed thereupon are effective to modulate light throughput with curvature of the device, wherein the form of the repeating curves produces a desired circumferential orientation and axial placement of light loss with respect to the device, such that the loss geometry produces modulation of the light indicative of the position and orientation of the device.

19. A measuring device according to claim 18 wherein the enhanced losses occur in only an axial portion or portions of one of said loss zones that would lose light uniformly along the entire loss zone when the fiber is straight and unformed.

20. A measuring device according to claim 19 wherein the said one loss zone is a thin axial band on a fiber when it is straight and unformed.

21. A measuring device according to claim 18 wherein said one of said loss zone is a circumferential band on a fiber when it is straight and unformed.

22. A measuring device according to claim 19 wherein the majority of the loss of a given fiber occurs at the same circumferential orientation at repeating intervals along the device, with the same spatial frequency as that of the cyclically repeating curves, wherein the repeating loss zones are used to create a spatially distributed sensing zone to capture an average reading of bend and twist along said zone.

23. A measuring device according to claim 14, wherein the member is in the form of a rope largely made up of said formed fibers, which formed fibers are helical and provide strands of said rope.

24. A measuring device according to claim 23, wherein said fibers are wound around a central core which provides part of the tensile strength of the member.

25. A measuring device according to claim 23, wherein at least one portion of the rope is provided with enhanced twist which is greater than the twist of parts of the rope between said portions.

26. A measuring device according to claim 25, wherein the portion with enhanced twist occupies an axial distance equal to the length occupied by one complete turn of the helical form of any one fiber within the portion having enhanced twist, or an integer multiple of said length.

27. A measuring device according to claim 1, wherein said fibers include a first set of fibers helically wound in one direction and a set of fibers helically wound in the opposite direction, the fibers of the two sets being interwoven with each other, so that said member is in the form of a braided structure.

28. A measuring device as in claim 1 wherein the member is in the form of a ribbon having a longitudinal dimension, said formed fibers including sinuous fibers connected side-by-side in the plane of the ribbon, the member being substantially limited to bending along its length only about axes which lie in the plane of the ribbon and which are transverse to the longitudinal dimension of the member, while the member is also free to twist.

29. A measuring device comprised of multiple ribbons according to claim 28 wherein the constituent ribbons are interleaved on alternate wavelengths of their sinuations.

30. A measuring device according to claim 28, wherein said ribbon is wound into helical form.

31. A measuring device according to claim 1, wherein said sensor is wound or sinuated in known relationship to features on a body to be measured, wherein the mathematical model of the turns and sinuations of the sensor is used to locate and scale similar features upon a mathematical model of the body being measured.

32. A measuring device according to claim 14, wherein the member is in the form of a woven or knitted fabric largely made up of said formed fibers.

33. A measuring device according to claim 32, wherein said member is in the form of a flexible sheet made up of a first set of said formed fibers extending in a first direction and a second set of said formed fibers extending across said fibers of the first set and being interwoven or interlaced with the fibers of the first set.

34. A measuring device according to claim 33, wherein the member is in the form of a woven sheet formed with a warp of said fibers of the first set and a weft of said fibers of the second set.

35. A measuring device according to claim 33, wherein the member is in the form of a knitted sheet formed from said formed fibers.

36. A measuring device according to claim 1, wherein each formed fiber has only one of said sensing portions.

37. A measuring device according to claim 1 wherein said fibers are optical fibers having reversing loops and wherein the fibers are sensitive to their state of curvature in the region of the loops.

38. A measuring tool for providing data corresponding to a geometric configuration in space comprising:
　(1) a flexible, compliant, measurement member extending along a medial axis or plane and capable of bending in at least one degree of freedom, said member having spaced flexure sensors at known locations distributed on said member and separated by flexure sensor spacing intervals to provide flexure signals indicating the local state of flexure present at said locations;
　(2) sensor data processing means coupled to the flexure sensors for receiving flexure signals therefrom and for presenting data on the geometric configuration of the member in three dimensional space, said data processing means operating by interpolating or extrapolating the geometric configuration of the member from the flexure signals provided by the flexure sensors and the spacings intervals between such sensors;
　wherein the measurement member comprises a multiplicity of formed fibers, such fibers being non-straight when the medial axis or plane of the member is respectively straight or flat, said formed fibers including sensing fibers having sensing portions which provide said flexure sensors, the sensing portions of different fibers being located at differing distances along said fibers so as to be located at said sensor spacing intervals, said formed fibers being in mutually supporting relationship, as by continuous or repeated contact with each other, so as to contribute materially to the strength or stability of the member, the overall form of the measurement member being maintained substantially by the form of the said formed fibers, alone or by their continuous or repeated contact with each other, to provide the strength or stability of the member.

39. A measuring device according to claim 10, wherein said formed optical fibers include fibers which maintain a non-straight form by reason of pre-twisting processes which produce permanent deformation of the fibers.

* * * * *